US012802181B2

(12) United States Patent
Jin et al.

(10) Patent No.: US 12,802,181 B2
(45) Date of Patent: Nov. 17, 2026

(54) ARTIFICIAL INTELLIGENCE-ENHANCED MICROSCOPE AND USE THEREOF

(71) Applicants: William Marsh Rice University, Houston, TX (US); THE BOARD OF REGENTS OF THE UNIVERSITY OF TEXAS SYSTEM, Austin, TX (US)

(72) Inventors: Lingbo Jin, Houston, TX (US); Yubo Tang, Houston, TX (US); Jackson Coole, Houston, TX (US); Melody Tan, Houston, TX (US); Xuan Zhao, Houston, TX (US); Hawraa Badaoui, Austin, TX (US); Jacob Robinson, Houston, TX (US); Michelle Williams, Austin, TX (US); Nadarajah Vigneswaran, Austin, TX (US); Ann Gillenwater, Austin, TX (US); Rebecca Richards-Kortum, Houston, TX (US); Ashok Veeraraghavan, Houston, TX (US)

(73) Assignees: William Marsh Rice University, Houston, TX (US); The Board Of Regents Of The University Of Texas System, Austin, TX (US)

( * ) Notice: Subject to any disclaimer, the term of this patent is extended or adjusted under 35 U.S.C. 154(b) by 0 days.

(21) Appl. No.: 19/091,346

(22) Filed: Mar. 26, 2025

(65) Prior Publication Data

US 2025/0308002 A1 Oct. 2, 2025

Related U.S. Application Data

(60) Provisional application No. 63/570,144, filed on Mar. 26, 2024.

(51) Int. Cl.
*G06T 7/00* (2017.01)
*A61B 5/00* (2006.01)
(Continued)

(52) U.S. Cl.
CPC .............. *G06T 5/73* (2024.01); *A61B 5/0071* (2013.01); *G06T 5/60* (2024.01); *G06T 7/0012* (2013.01);
(Continued)

(58) Field of Classification Search
CPC .... G06T 5/73; G06T 5/60; G06T 7/00; G06T 7/0012; G06T 2207/10056;
(Continued)

(56) References Cited

U.S. PATENT DOCUMENTS 8,143,600 B2 * 3/2012 Seibel ................ G01N 15/1436 250/461.2
11,482,320 B2 * 10/2022 Klaiman ............... G06T 7/0012
(Continued)

OTHER PUBLICATIONS

Xiao, S., Tseng, H., Gritton, H., Han, X. & Mertz, J., "Video-Rate Volumetric Neuronal Imaging Using 3d Targeted Illumination", May 21, 2018, 1-10, 8:7921, Scientific Reports.
(Continued)

*Primary Examiner* — Trang U Tran
(74) *Attorney, Agent, or Firm* — Osha Bergman Watanabe & Burton LLP

(57) ABSTRACT

A system includes a microscope and computer system communicably coupled together. The microscope includes a camera, phase mask, and ultraviolet source. The phase mask is disposed within a view of the camera. The microscope is configured to scatter a light illuminating a tissue by emitting, using the ultraviolet source, an ultraviolet radiation towards the tissue and obtain, using the phase mask and the camera, an image of an illuminated surface of the tissue. The tissue
(Continued)

includes at least one diagnostic feature. The image is within a predefined depth of field, inclusive, and includes a manifestation of the at least one diagnostic feature. The computer system is configured to determine a deblurred image from a trained first artificial intelligence model based on the image.

15 Claims, 24 Drawing Sheets

(51) Int. Cl.
*G06T 5/60* (2024.01)
*G06T 5/73* (2024.01)

(52) U.S. Cl.
CPC ............... *G06T 2207/10056* (2013.01); *G06T 2207/20081* (2013.01); *G06T 2207/30024* (2013.01)

(58) Field of Classification Search
CPC . G06T 2207/20081; G06T 2207/30024; A61B 5/0071
USPC ........................................................ 348/79
See application file for complete search history.

(56) References Cited

U.S. PATENT DOCUMENTS

| | | | | |
|---|---|---|---|---|
| 11,995,810 | B2 * | 5/2024 | Lau | G01N 1/30 |
| 12,475,564 | B2 * | 11/2025 | Ianni | G06T 7/0012 |
| 12,629,001 | B2 * | 5/2026 | Kim | A61B 1/000096 |
| 12,670,703 | B2 * | 6/2026 | Freytag | G06T 7/0012 |
| 2025/0377536 | A1 * | 12/2025 | Veeraraghavan | G02B 27/0012 |

OTHER PUBLICATIONS

Xue, Y., Davison, I. G., Boas, D. A. & Tian, L., "Single-Shot 3d Wide-Field Fluorescence Imaging with a Computational Miniature Mesoscope", Oct. 21, 2020, 1-15, 6 : eabb7508, Science Advances.
Yanny, K. et al., "Miniscope3d: Optimized Single-Shot Miniature 3d Fluorescence Microscopy", 2020, 1-13, 9:171, Light: Science and Applications.
(Abstract) of Zhang, W. et al., "Merging Nucleus Datasets by Correlation-Based Cross-Training", 2023, 84, 102705, Med. Image Analalysis.
Zhu, J. Y., Park, T., Isola, P. & Efros, A. A., "Unpaired Image-To-Image Translation Using Cycle-Consistent Adversarial Networks", Aug. 24, 2020, Preprint at Http://Arxiv.Org/Abs/1703.10593.
Adams, J. K. et al., "In Vivo Lensless Microscopy via a Phase Mask Generating Diffraction Patterns with High-Contrast Contours", 2022, 617-628, vol. 6, Nat. Biomed. Eng.
Adams, J. K. et al., "Single-Frame 3d Fluorescence Microscopy with Ultraminiature Lensless Flatscope", 2017, 1-9, vol. 3, E1701548, Science Advances.
An Intro to H&E Staining: Protocol, Best Practices, Steps & More. Https://Www.Leicabiosystems.Com/Us/Knowledge-Pathway/He-Staining-Overview-A-Guide-To-Best-Practices/.
Ashman, K. et al., "A Camera-Assisted Pathology Microscope to Capture the Lost Data in Clinical Glass Slide Diagnosis", Sep. 3, 2022, BioRxiv Preprint Https://Doi.Org/10.1101/2022.08.31.506042 (2022).
Assayag, O. et al., "Large Field, High Resolution Full-Field Optical Coherence Tomography", 2014, 455-468, vol. 13, Technology in Cancer Research and Treatment.
Baek, J., "Transfer Efficiency and Depth Invariance in Computational Cameras", Mar. 29, 2010, 1-8, IEEE International Conference on Computational Photography, Doi:10.1109/Iccphot.2010.5585098.
Bai, B. et al., "Deep Learning-Enabled Virtual Histological Staining of Biological Samples", 2023, 12:57, Light: Science & Applications.
Bay, H., Tuytelaars, T. & Van Gool, L., "Surf: Speeded Up Robust Features", 2006, 404-417, In Computer Vision—ECCV, (Eds. Leonardis, A., Bischof, H. & Pinz, A.), Springer, Berlin, Heidelberg, Doi:10.1007/11744023_32.
Besseling, T., Jose, J. & Blaaderen, A. V., Methods to Calibrate and Scale Axial Distances in Confocal Microscopy as a Function of Refractive Index, 2015, 142-150, vol. 257(2), Journal of Microscopy.
(Manuscript) of Cao, R. et al., Label-Free Intraoperative Histology of Bone Tissue via Deep-Learning-Assisted Ultraviolet Photoacoustic Microscopy, 2023, 124-134, 7(2), Nat Biomed Eng. Author Manuscript.
Chen, Y., Liu, H., Zhou, Y., Kuang, F.-L. & Li, L., "Extended the Depth of Field and Zoom Microscope with Varifocal Lens", 2022, 12:11015, Scientific Reports.
Chen, Z., Yu, W., Wong, I. H. M. & Wong, T. T. W., "Deep-Learning-Assisted Microscopy with Ultraviolet Surface Excitation for Rapid Slide-Free Histological Imaging", 2021, 12, 5920-5938, Biomed. Opt. Express.
De Bel, T., Bokhorst, J.-M., Van Der Laak, J. & Litjens, G., "Residual Cyclegan for Robust Domain Transformation of Histopathological Tissue Slides", 2021, 70, 102004, Med. Image Analysis.
Dinardo, L. J., Lin, J., Karageorge, L. S. & Powers, C. N., "Accuracy, Utility, And Cost of Frozen Section Margins in Head and Neck Cancer Surgery", 2000, 1773-1776, 110, The Laryngoscope.
(Manuscript) of Fereidouni, F. et al., "Microscopy with Ultraviolet Surface Excitation for Rapid Slide-Free Histology", 2017, 957-966, 1, Nat. Biomed. Eng.
Ferlay, J. et al., "Cancer Statistics for the Year 2020: An Overview", 2021, 778-789, 149, Int. J. Cancer, Cancer Epidemiology.
Fontelo, P., Faustorilla, J., Gavino, A. & Marcelo, A. "Digital Pathology—Implementation Challenges in Low-Resource Countries", 2012, 35, 31-36, Analytical Cellular Pathology.
Ghanekar, B. et al., "PS2F: Polarized Spiral Point Spread Function for Single-Shot 3d Sensing", 2022, Preprint Https://Doi.Org/10.48550/Arxiv.2207.00945 (2022).
Giacomelli, M. G. et al., "Virtual Hematoxylin and Eosin Transillumination Microscopy Using Epi-Fluorescence Imaging", 2016, 11, E0159337, Plos One.
(Manuscript) of Glaser, A. K. et al., "Light-Sheet Microscopy for Slide-Free Non-Destructive Pathology of Large Clinical Specimens", 2017, 0084, 1, Nat. Biomed. Eng.
Goodman, J. W., "Introduction to Fourier Optics", 2005, Roberts and Company Publishers.
Isola, P., Zhu, J.-Y., Zhou, T. & Efros, A. A., "Unpaired Image-To-Image Translation With Conditional Adversarial Networks", 2018, Preprint Https://Doi.Org/10.48550/Arxiv.1611.07004 (2018).
Jegou, H., Douze, M. & Schmid, C., "Hamming Embedding And Weak Geometric Consistency for Large Scale Image Search", 2008, 304-317, In Computer Vision—ECCV (Eds. Forsyth, D., Torr, P. & Zisserman, A.), Springer, Berlin, Heidelberg Doi:10.1007/978-3-540-88682-2_24.
Jin, L. et al., "Deep Learning Extended Depth-Of-Field Microscope for Fast and Slide-Free Histology", 2020, 33051-33060, 117, Proc. Natl. Acad. Sci.
Kingma, D. P. & Ba, J., ADAM: A Method for Stochastic Optimization, 2017, Preprint at Https://Doi.Org/10.48550/Arxiv.1412.6980 (2017).
Krupinski, E. A., Johnson, J. P., Jaw, S., Graham, A. R. & Weinstein, R. S., "Compressing Pathology Whole-Slide Images Using a Human and Model Observer Evaluation", 2012, 17, 3, J. Pathol. Inform.
Lambert, J., Liu, Z., Sener, O., Hays, J. & Koltun, V., "MSEG: A Composite Dataset for Multi-Domain Semantic Segmentation", 2021, Preprint Https://Doi.Org/10.48550/Arxiv.2112.13762 (2021).
Mao, X. et al., "Least Squares Generative Adversarial Networks", 2017, Preprint Http://Arxiv.Org/Abs/1611.04076 (2017).
Marini, N. et al., "Data-Driven Color Augmentation for H&E Stained Images in Computational Pathology", Jan. 3, 2023, 1-12, 14, 100183, Journal of Pathology Informatics.
Martell, M. T. et al., "Deep Learning-Enabled Realistic Virtual Histology with Ultraviolet Photoacoustic Remote Sensing Microscopy", Sep. 25, 2023, 1-17, 14:5967, Nature Communications.

(56) References Cited

OTHER PUBLICATIONS

Abstract) of Meng, T., Jing, X., Yan, Z. & Pedrycz, W. A, "Survey on Machine Learning for Data Fusion", 2020, 115-129, 57, Inf. Fusion.
Miller, K. D. et al., "Cancer Treatment and Survivorship Statistics, 2022", Sep. 2022, 409-436, vol. 72, No. 5, Ca Cancer J. Clin.
Neary-Zajiczek, L. et al., "Minimum Resolution Requirements of Digital Pathology Images for Accurate Classification", Jul. 13, 2023, 1-13, 89, 102891, Medical Image Analysis.
Nehme, E. et al., "Deepstorm3d: Dense 3d Localization Microscopy and Psf Design by Deep Learning", Jul. 1, 2020, 1-19, 17(7): 734-740, Nat. Methods.
Paoli, J., Smedh, M. & Ericson, M. B., "Multiphoton Laser Scanning Microscopy—A Novel Diagnostic Method for Superficial Skin Cancers", 2009, 190-195, 28, Seminars in Cutaneous Medicine and Surgery.
Patel, A. et al., "Contemporary Whole Slide Imaging Devices and Their Applications Within the Modern Pathology Department: A Selected Hardware Review", Dec. 9, 2021, 1-27, vol. 12, Issue 1, 50, Journal of Pathology Informatics.
Patel, Y. G. et al., "Confocal Reflectance Mosaicing of Basal Cell Carcinomas in Mohs Surgical Skin Excisions", May 2007, 12(3), 034027, Journal of Biomedical Optics.
Pavani, S. R. P. et al., "Three-Dimensional, Single-Molecule Fluorescence Imaging Beyond the Diffraction Limit by Using a Double-Helix Point Spread Function", Mar. 3, 2009, 2995-2999, vol. 106, No. 9, Proceedings of the National Academy of Sciences.
Pitrone, P. G. et al., "OpenSPIM: An Open-Access Light-Sheet Microscopy Platform", Jul. 2013, 1-5, 10(7): 598-599, Nat. Methods.
Ragazzi, M. et al., "Fluorescence Confocal Microscopy for Pathologists", Sep. 13, 2013, 460-471, 27, Modern Pathology.
(Abstract) of Rivenson, Y. et al., "Virtual Histological Staining of Unlabelled Tissue-Autofluorescence Images via Deep Learning", 2019, 466-477, 3, Nat. Biomed. Eng.
(Abstract) of Wong, E., Axibal, E. & Brown, M., "Mohs Micrographic Surgery" 2019, 15-34, 27, Facial Plast. Surg. Clin. N. Am.
Shain, W. J., Vickers, N. A., Goldberg, B. B., Bifano, T. & Mertz, J., "Extended Depth-Of-Field Microscopy with a High-Speed Deformable Mirror", Feb. 8, 2017, 995-998, 42, Optics Letters.
Stirling, D. R. et al., "Cellprofiler 4: Improvements in Speed, Utility and Usability", 2021, 1-11, 22:433, BMC Bioinformatics.
(Abstract) of Sutton, E. & Hanke, C. W., "Microscope Use in Mohs Micrographic Surgery: A Survey of Current and Former Mohs Surgery Fellowship Directors", 2022, 786-787, 48, Dermatol. Surg. Off. Publ. Am. Soc. Dermatol. Surg. AI.
Tian, F., Hu, J. & Yang, W., "Geomscope: Large Field-Of-View 3d Lensless Microscopy with Low Computational Complexity", Aug. 2021, 1-26, 15, 2100072, Laser Photonics Rev.
Tkaczyk, E. R., "Innovations and Developments in Dermatologic Non-Invasive Optical Imaging and Potential Clinical Applications", 2017, 1-19, Suppl 218, 5-13, Acta Derm. Venereol.
Wang, Y. M., Judkewitz, B., Dimarzio, C. A. & Yang, C., "Deep-Tissue Focal Fluorescence Imaging with Digitally Time-Reversed Ultrasound-Encoded Light", Jun. 26, 2012, 1-8, Nature Communications.
Wang, Z., Simoncelli, E. P. & Bovik, A. C., "Multiscale Structural Similarity for Image Quality Assessment", Nov. 2003, 1398-1402, Proceedings of the 37th IEEE Asilomar Conference on Signals, Systems and Computers, Pacific Grove, CA, IEEE.

* cited by examiner

ARTIFICIAL INTELLIGENCE-ENHANCED MICROSCOPE AND USE THEREOF

CROSS REFERENCE

This application claims priority to U.S. provisional patent application No. 63/570,144, filed Mar. 26, 2024, which is herein incorporated by reference.

STATEMENT REGARDING FEDERALLY-SPONSORED RESEARCH

This invention was made with government support under Grant No. 1730574 awarded by the National Science Foundation, Grant No. R01DE032051 awarded by the National Institutes of Health, and Grant Nos. N66001-17-C-4012 and N66001-19-C-4020 awarded by the Department of Defense. The government has certain rights in the invention.

BACKGROUND

Histopathology plays a critical role in the diagnosis and surgical management of disease, such as cancer. However, access to histopathology services, especially frozen-section pathology during surgery, is limited in resource-constrained settings because preparing slides from tissue is time-consuming, is labor-intensive, and requires expensive infrastructure. Accordingly, there is a need to develop histopathology services that do not rely on slides for diagnosis and surgical management.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a system. The system includes a microscope and computer system communicably coupled together. The microscope includes a camera, phase mask, and ultraviolet source. The phase mask is disposed within a view of the camera. The microscope is configured to scatter a light illuminating a tissue by emitting, using the ultraviolet source, an ultraviolet radiation towards the tissue and obtain, using the phase mask and the camera, an image of an illuminated surface of the tissue. The tissue includes at least one diagnostic feature. The image is within a predefined depth of field, inclusive, and includes a manifestation of the at least one diagnostic feature. The computer system is configured to determine a deblurred image from a trained first artificial intelligence model based on the image.

In general, in another aspect, embodiments relate to a method. The method includes scattering a light illuminating a tissue by emitting an ultraviolet radiation towards the tissue. The tissue includes at least one diagnostic feature. The method further includes obtaining an image of an illuminated surface of the tissue. The image is within a predefined depth of field, inclusive, and includes a manifestation of the at least one diagnostic feature. The method still further includes determining a deblurred image from a trained first artificial intelligence model based on the image.

In general, in still another aspect, embodiments relate to a method. The method includes obtaining focused training images within a predefined depth of field, inclusive, and defining a height map for a phase mask. Each of the focused training images corresponds to each depth within the predefined depth of field. The method further includes training a first artificial intelligence model. Training includes, until a predefined criterion is met, determining a point-spread function for each depth using the height map, determining blurred training images by convolving each of the focused training images that corresponds to each depth with the point-spread function for each depth, determining predicted deblurred images from the first artificial intelligence model based on the blurred training images, and updating the height map and the first artificial intelligence model based on a loss function between the focused training images and the predicted deblurred images. The first artificial intelligence model is trained to determine a predicted deblurred image in response to an input image obtained using the phase mask.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
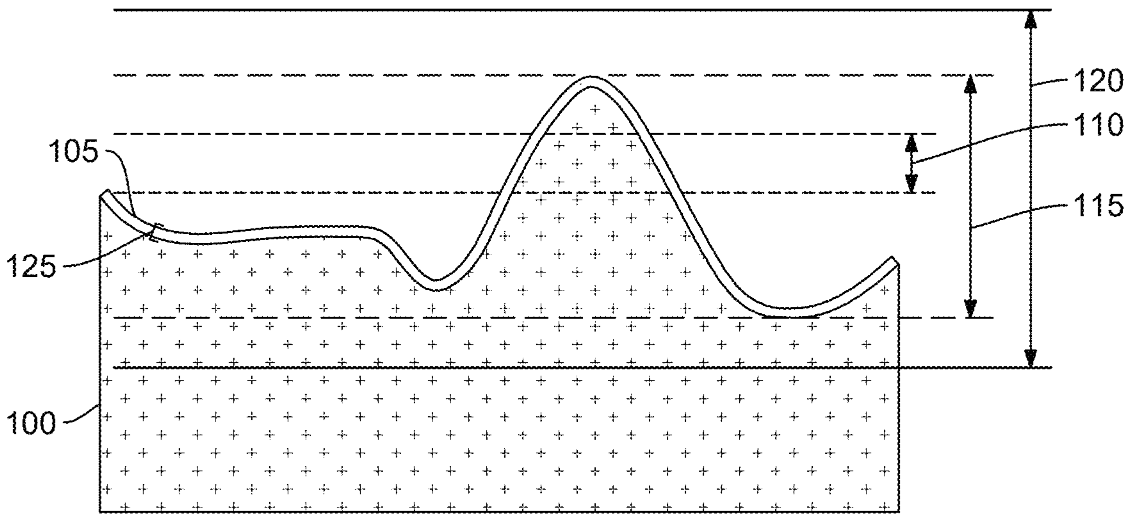
FIG. 1 illustrates depths of field in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a sonic waveform" includes reference to one or more of such waveforms.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

In the following description of FIGS. 1-30, any component described regarding a figure, in various embodiments disclosed herein, may be equivalent to one or more like-named components described regarding any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described regarding a corresponding like-named component in any other figure.

Systems and methods are disclosed herein. The systems include a microscope and computer system communicably coupled together. The microscope includes a phase mask and ultraviolet (UV) source. The microscope is configured to obtain an image of a tissue of a patient. Slides of thinly-sliced samples of the tissue need not be prepared prior to imaging the tissue using the microscope. Accordingly, the tissue may be in-vivo tissue or resected tissue that is resected from the patient. As such, in some embodiments, the microscope, in part, may be disposed near or within the in-vivo tissue. In other embodiments, the entire resected tissue may be placed on a stage of the microscope. The methods include deblurring the image of the tissue using the phase mask and one or more trained first artificial intelligence (AI) models. Each first AI model may deblur manifestations of a feature within the image where the feature fluoresces at a unique wavelength. In some embodiments, the methods further include virtually-staining the deblurred image using a trained second AI model.

Hereinafter, the terms "blurry" and "crisp" are used antonymously to describe image quality. That is, if an image is less blurry, the image is also more crisp. If an image is less crisp, the image is also more blurry. The term "deblurred" then refers to an image being less blurry and more crisp. Further, hereinafter, the terms "crisp," "focused," and "clear" are used synonymously. However, referring to an image as crisp, focused, or clear does not mean the image is perfectly crisp, focused, or clear, but increasingly crisp, focused, or clear compared to the image prior to, for example, some processing step. A crisp, focused, or clear image is of a higher quality than a blurry image. It is thus desirable to determine a crisp, focused, or clear image over a blurry image such that features within the tissue that manifest within the image are clearly identifiable and, thus, clinically useful.

The disclosed systems have several advantages over conventional systems that obtain a conventional image using a conventional microscope. Because the disclosed microscope includes a phase mask, the disclosed microscope is configured to obtain an image that is less blurry than the conventional image and over a larger depth-of-field (DOF) than the conventional microscope. FIG. 1 illustrates this point in accordance with one or more embodiments. FIG. 1 shows a tissue 100 with a highly-irregular or nonlinear surface 105. With the conventional microscope, or rather any imaging modality, there is a tradeoff between DOF and resolution. The higher the resolution, the closer to the surface 105 the DOF is. FIG. 1 illustrates this as a conventional DOF 110. The lower the resolution, the further from the surface 105 (i.e., deeper) the DOF is. Accordingly, the conventional DOF 110 of the conventional microscope may not be able to obtain a focused image of the entire surface 105 of the tissue 100 when the height range 115 of the surface 105 of the tissue 100 is larger than and, thus, somewhat outside of the conventional DOF 110 as FIG. 1 illustrates. This may not be a problem when the tissue 100 is thinly sectioned (such that the height range of the section is within the conventional DOF 110) and placed on a slide for obtaining the conventional image. However, slide preparation is time-consuming, is labor-intensive, and requires expensive infrastructure. The disclosed systems and methods avoid the use of slides. However, avoiding the use of slides causes the problem that the height range 115 of the surface 105 the tissue 100 may not always be within the conventional DOF 110. The disclosed phase mask increases the DOF (hereinafter "predefined DOF" 120, extended DOF (EDOF), or target DOF) such that crisper images are obtained within the predefined DOF 120 than they would be with the conventional microscope (i.e., without the phase mask). In turn, an image of the entire surface 105—even if highly irregular—of the tissue 100 can be obtained when the height range 115 of the surface 105 of the tissue 100 is within the predefined DOF 120 as FIG. 1 illustrates.

It is further advantageous for the disclosed microscope to include the UV source. The UV source allows the disclosed microscope to obtain the image of the surface 105 of the tissue 100 only. If the disclosed microscope excluding the UV source obtains an image of the tissue 100, the image is a projection of the entire tissue 100. Accordingly, features of the entire tissue 100 that manifest in the image overlap or overlay with one another. Further, features increasingly outside of the predefined DOF 120 will be increasing blurry in the image. This limits clinical use of the image because the manifestation of clinically-useful features (hereinafter also "diagnostic features") may be occluded or hidden by other features. Inclusion of the UV source limits the image to the surface 105 of the tissue 100. This is commonly denoted "UV surface excitation." To only excite the surface 105, the UV source is configured to emit UV radiation (colloquially "UV light"). By emitting the UV radiation towards the tissue 100, the UV radiation scatters a light illuminating the tissue 100. In doing so, the UV radiation limits the intensity of light illuminating the tissue 100 such that the disclosed microscope can only obtain an image of the surface 105 of the tissue 100. Accordingly, the image would clearly include manifestations of features not occluded by other features that exist deeper within the tissue 100 that are no longer being imaged.

Herein, the term "surface" 105 refers to being at and just below the surface 105 of a tissue 100 based on a predefined depth 125 below the surface 105. The predefined depth 125 follows the nonlinearity of the surface 105. The predefined depth 125 may be on the order of micrometers (μm), such as between 10 μm to 20 μm, inclusive. The region of the tissue 100 ranging from the surface 105 to the predefined depth 125 may be generically denoted a "surface of the tissue" or "illuminated surface of the tissue."

The disclosed methods also have several advantages over conventional methods used to deblur the image. The disclosed methods rely on the trained first AI model. The first AI model is trained to deblur the image no matter the depth within the predefined DOF 120, inclusive, that the image is obtained in. Further, the first AI model is trained to determine a height map of the phase mask prior to the phase mask being disposed within the microscope and used to obtain the image. Accordingly, the training process offers at least two advantages or improvements. One, the training process determines the height map of the phase mask (i.e., the design of the phase mask) that will allow the microscope with phase mask to obtain less blurry images of the tissue 100 when imaging within the predefined DOF 120 compared to the conventional microscope. Second, the trained first AI model then further reduces the blurriness of the obtained image to determine a deblurred image.

In some embodiments, the disclosed methods may rely on the trained second AI model. The second AI model is trained to virtually-stain the deblurred image. In doing so, physically staining the tissue 100 may be reduced or not be needed.

Other advantages will become clear as the disclosed systems and methods are described in detail below.

Figure 2:
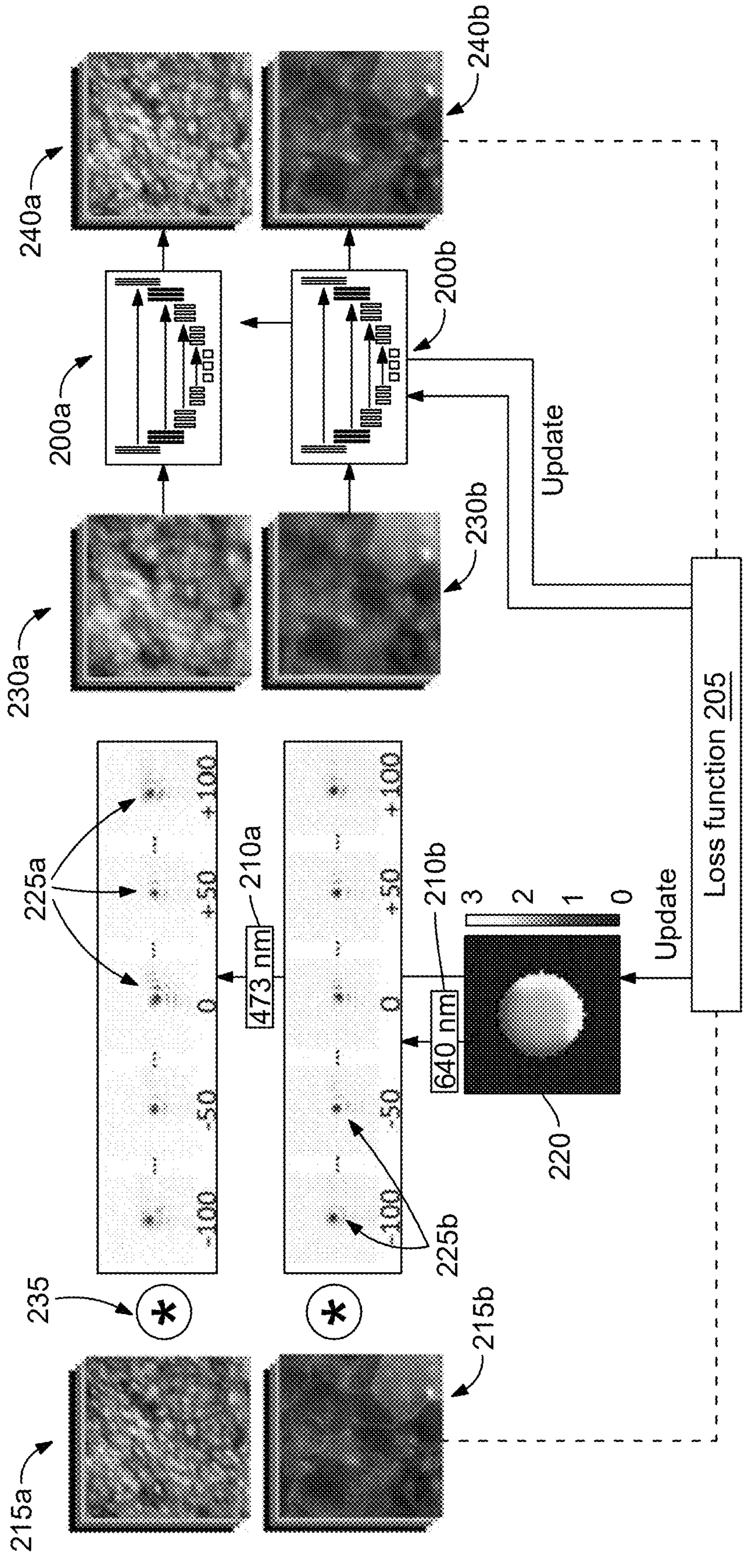
FIG. 2 illustrates a method of training a first artificial intelligence (AI) model in accordance with one or more embodiments.

FIG. 2 illustrates a method of training two first AI models 200*a, b* in accordance with one or more embodiments. However, prior to discussing how each first AI model 200*a, b* is trained, the term "artificial intelligence" and the architecture of AI models, in general, should be understood.

AI, broadly defined, is the extraction of patterns and insights from data. The phrases "artificial intelligence," "machine learning," "deep learning," and "pattern recognition" are often convoluted, interchanged, and used synonymously throughout the literature. This ambiguity arises because the field of "extracting patterns and insights from data" was developed simultaneously and disjointedly among a number of classical arts like mathematics, statistics, and computer science. For consistency, the terms AI, AI-learned, and deep-learned are adopted herein. However, one skilled in the art will recognize that the concepts and methods detailed hereafter are not limited by this choice of nomenclature.

AI models may include, but are not limited to, generalized linear models, Bayesian regression, random forests, and deep models such as neural networks (NN), convolutional neural networks (CNN), and recurrent neural networks (RNN). AI models, whether they are considered deep or not, are usually associated with additional "hyperparameters" which further describe the AI model. Hyperparameters may include, but are not limited to, the number of layers in the NN, choice of activation functions, inclusion of batch normalization layers, and regularization strength. It is noted that in the context of AI, the regularization of the AI model refers to a penalty applied to a loss function 205 of the AI model. Commonly, in the literature, the selection of hyperparameters surrounding the AI model is referred to as selecting the model "architecture." Once the AI model and associated architecture are selected, the AI model is trained to perform a task, the performance of the AI model is evaluated, and the AI model is used for prediction (i.e., the AI model is deployed for use).

The AI model may be a CNN. A CNN may be more readily understood as a specialized NN. Thus, a cursory introduction to an NN and CNN are provided herein. However, it is noted that many variations of an NN and CNN exist. Therefore, one with ordinary skill in the art will recognize that any variation of the NN or CNN (or any other AI model) may be employed without departing from the scope of this disclosure. Further, it is emphasized that the following discussions of an NN and CNN are basic summaries and should not be considered limiting.

At a high level, an NN may be graphically depicted as being composed of nodes and edges. The nodes may be grouped to form layers. The edges connect the nodes. Edges may connect, or not connect, to any node(s) regardless of which layer the node is in. That is, the nodes may be sparsely and/or densely connected. An NN will have at least two layers, where the first layer is considered the "input layer" and the last layer is the "output layer." Any intermediate layer is usually described as a "hidden layer." An NN may have zero or more hidden layers. An NN with at least one hidden layer may be described as a "deep" NN or "deep-learning model." In general, an NN may have more than one node in the output layer. In these cases, the NN may be referred to as a "multi-target" or "multi-output" network.

Nodes and edges carry additional associations. Namely, every edge is associated with a numerical value. The edge numerical values, or even the edges themselves, are often referred to as "weights" or "parameters." While training an NN, numerical values are assigned to each edge. Additionally, every node is associated with a numerical variable and an activation function. Activation functions are not limited to any functional class, but traditionally follow the form:

$$A = f\left(\sum_{i\in(incoming)}[(\text{node value})_i\,(\text{edge value})_i]\right),$$

where i is an index that spans the set of "incoming" nodes and edges and f is a user-defined function. Incoming nodes are those that, when viewed as a graph, have directed arrows that point to the node where the numerical value is being computed. Some functions for $f$ may include the linear function $f(x)=x$, sigmoid function $$f(x) = \frac{1}{1+e^{-x}},$$

and rectified linear unit function $f(x)=\max(0,x)$. However, many additional functions are commonly employed. Every node in an NN may have a different associated activation function. Often, as a shorthand, activation functions are described by the function $f$ by which it is composed. That is, an activation function composed of a linear function $f$ may simply be referred to as a linear activation function without undue ambiguity.

When the NN receives an input, the input is propagated through the network according to the activation functions and incoming node values and edge values to compute a value for each node. That is, the numerical value for each node may change for each received input. Occasionally, nodes are assigned fixed numerical values, such as the value of 1, which are not affected by the input or altered according to edge values and activation functions. Fixed nodes are often referred to as "biases" or "bias nodes."

In some implementations, an NN may contain specialized layers, such as a normalization layer or additional connection procedures like concatenation. One skilled in the art will appreciate that these alterations do not exceed the scope of this disclosure.

As noted, the training procedure for the NN comprises assigning values to the edges. To begin training, the edges are assigned initial values. These values may be assigned randomly, assigned according to a prescribed distribution, assigned manually, or by some other assignment mechanism. Once edge values have been initialized, the NN may act as a function, such that it may receive inputs and produce an output. As such, at least one input is propagated through the NN to produce an output.

Training data is provided to the NN. Generally, though not always, training data consists of paired data, where each pair includes an input and associated target output (hereinafter simply "target"). The targets represent the "ground truth," or the otherwise desired output upon processing the inputs. In the context of the instant disclosure, an input is an image (that may be blurred) and its associated target is a predicted deblurred image. During training, the NN processes at least one input from the training data and produces at least one output. Each NN output is compared to the associated target. The comparison of the NN output to the target is typically performed by a "loss function" 205 though other names for this comparison function include an "error function," "misfit function," and "cost function." Many types of loss functions 205 are available, such as the mean-squared-error function. However, the general characteristic of the loss function 205 is that the loss function 205 provides a numerical evaluation of the similarity between the NN output (i.e., predicted deblurred images) and the associated target (i.e., focused training images). The loss function 205 may also be constructed to impose additional constraints on the values assumed by the edges, such as by adding a penalty term, which may be physics-based, or a regularization term. Generally, the goal of a training procedure is to alter the edge values to promote similarity between the NN output and associated target over the training data. Thus, the loss function 205 is used to guide changes made to the edge values through a process called "backpropagation."

While a full review of the backpropagation process exceeds the scope of this disclosure, a brief summary is provided. Backpropagation consists of computing the gradient of the loss function 205 over the edge values. The gradient indicates the direction of change in the edge values that results in the greatest change to the loss function 205. Because the gradient is local to the current edge values, the edge values are typically updated by a "step" in the direction indicated by the gradient. The step size is often referred to as the "learning rate" and need not remain fixed during the iterative training process. Additionally, the step size and direction may be informed by previously-seen edge values or previously-computed gradients. Such methods for determining the step direction are usually referred to as "momentum" based methods.

Once the edge values have been updated or altered from their initial values through a backpropagation step, the NN will likely produce different outputs. Thus, the procedure of propagating at least one input through the NN, comparing the NN output with the associated target with the loss function 205, computing the gradient of the loss function 205 with respect to the edge values, and updating the edge values with a step guided by the gradient, is repeated iteratively until a predefined criterion is met. Common termination criteria include reaching a fixed number of edge updates, otherwise known as an iteration counter, a diminishing learning rate, noting no appreciable change in the loss function 205 between iterations, and reaching a specified performance metric as evaluated on the training data or separate hold-out training data. Once the predefined criterion is met and the edge values are no longer intended to be altered, the NN is said to be "trained."

A CNN is similar to an NN in that it can technically be graphically represented by a series of edges and nodes grouped to form layers. However, it is more informative to view a CNN as structural groupings of weights, where the term "structural" indicates that the weights within a group have a relationship. CNNs are widely applied when the inputs also have a structural relationship, for example, a spatial relationship where one input is always considered "to the left" of another input. Images have such a structural relationship because each data element, or pixel, in an image has a spatial relationship to every other pixel in the image. Consequently, a CNN is an intuitive choice for processing images.

A structural grouping of weights is herein referred to as a "filter." The number of weights in a filter is typically much less than the number of inputs, where here the number of inputs refers to the number of pixels in an input image. In a CNN, the filters can be thought as "sliding" over, or convolving with, the inputs to form an intermediate output or intermediate representation of the inputs that retain a structural relationship. Like a NN, the intermediate outputs are often further processed with an activation function. Many filters may be applied to the inputs to form many intermediate representations. Additional filters may be formed to operate on the intermediate representations creating more intermediate representations. This process may be repeated as prescribed by the architecture of the CNN. There is a "final" group of intermediate representations where filters do not act on these intermediate representations. In some instances, the structural relationship of the final intermediate representations is ablated-a process known as "flattening." The flattened representation may be passed to an NN to produce a final output. Note, in this context, the NN is still considered part of the CNN. Like the NN, the CNN is trained using backpropagation.

Returning to FIG. 2, FIG. 2 illustrates two first AI models 200*a, b* being trained in parallel. Each first AI model 200*a, b* may be or include a U-net CNN. The term U-net comes from the CNN being composed of an encoder CNN and decoder CNN connected by an intermediate connection block that, as shown in FIG. 2, forms the shape of the letter "U."

Each first AI model 200*a, b* is trained to determine a predicted deblurred image in response to an input image (hereinafter also simply "image") based on features of the input image fluorescing at a predefined wavelength 210*a, b*. These features may fluoresce at the predefined wavelength 210*a, b* because of a stain applied to the tissue that the focused training images 215*a, b* and input image are of, such as DAPI and Rhodamine B stains. FIG. 2 specifically illustrates one first AI model 200*a* being trained based on the predefined wavelength 210*a* of 473 nanometers (nm) such that the DAPI stain fluoresces and the other first AI model 200*b* being trained based on the predefined wavelength 210*b* of 640 nm such that the Rhodamine B stain fluoresces. A person of ordinary skill in the art will appreciate however that any stain and associated predefined wavelength 210*a, b* that the stain fluoresces at may be used without departing from the scope of the disclosure. This includes an absence of the use of a stain such that features autofluoresce at an associated predefined wavelength. Accordingly, the number of predefined wavelengths 210*a, b* corresponds to the number of channels of the disclosed microscope and number of first AI models 200*a, b*. For example, two predefined wavelengths 210*a, b* corresponds to a dual-channel microscope and two first AI models 200*a, b*.

Note there may be crosstalk between the channels of the microscope. Accordingly, each channel of the microscope may not exactly match or correspond to the red, green, and blue wavelengths (RGB) that a camera of the microscope are obtaining. Accordingly, the first AI models 200*a, b* may be robustly trained such that they may make adequate predictions in the presence of crosstalk.

Each first AI model 200*a, b* replaces the mathematical operation of deconvolution that is traditionally used to deblur an image for each channel. That is, traditionally, the image may be deconvolved with its point-spread function (PSF) for a given channel to determine or reconstruct a crisp or deblurred image compared to the image. Each first AI model 200*a, b* then offers an improvement over deconvolution because the PSF is not needed for each first AI model 200*a, b* to determine the predicted deblurred image. Further, training each first AI model 200*a, b* offers an improvement of determining the height map 220 for the phase mask of the disclosed microscope in tandem to training.

Prior to training each first AI model 200*a, b*, a portion of the training images is obtained. These training images include the focused training images 215*a, b*. The focused training images 215*a, b* may be images of any tissue including a collection of different tissues. In some embodiments, the tissues may be physically stained such that features of interest within the tissues fluoresce at the predefined wavelength 210*a, b*. In other embodiments, the tissues may not be stained such that features of interest autofluoresce at the predefined wavelength 210*a, b*. In some embodiments, the focused training images 215*a, b* may be images of slide-prepared tissue. In other embodiments, the focused training images 215*a, b* may be images of whole tissue where a UV source is used within a microscope to obtain each image of only the surface of the whole tissue as later described relative to FIG. 3. As such, focused training images 215*a, b* may vary in tissue type, stain, tissue size, and manifestation of features.

Furthermore, one or more of the focused training images 215*a, b* may be obtained at a depth within the predefined DOF 120. For example, if the predefined DOF is 200 micrometers (μm), inclusive (i.e., −100 μm to 100 μm as FIG. 1 illustrates), some focused training images 215*a, b* may be focused at the depth of −100 μm, −50 μm, 0 μm (i.e., central depth), 50 μm, and 100 μm (i.e., five depths).

For each iteration of training, the focused training images 215*a, b* at each depth are convolved with its corresponding PSF 225*a, b* for that depth to determine blurred training images 230*a, b*. FIG. 2 illustrates this for the five depths, where the convolution operator 235 is shown as. A person of ordinary skill in the art will appreciate that any number of depths within the predefined DOF 120 may be used and, accordingly, that number of corresponding PSFs 225*a, b* when training each first AI model 200*a, b*. It may be advantageous to include a large number of depths within the predefined DOF 120. In some embodiments, each PSF 225*a, b* is simulated for each iteration of training based on the current height map 220 for the phase mask of the microscope and the predefined wavelength 210*a, b*.

During each iteration of training, each first AI model 200*a, b* determines predicted deblurred images 240*a, b*. One focused training image 215*a, b* corresponds to one blurred training image 230*a, b* and, thus, one predicted deblurred image 240*a, b*. Accordingly, the training images are considered paired. The predicted deblurred images 240*a, b* are compared with the focused training images 215*a, b* based on the loss function 205. The value of the loss function 205 determines how the height map 220 for the phase mask and weights within each first AI model 200*a, b* are updated prior to performing the next iteration of training.

On the next iteration of training, the updated height map 220 is used to update the PSFs 225*a, b* and, in turn, update the blurred training images 230*a, b*. This iterative training process continues until the loss function 205 the predefined criterion is met. This occurs when the predicted deblurred images 240*a, b* substantially match the focused training images 215*a, b*. Once this occurs, each first AI model 200*a, b* is considered to be trained and the height map 220 considered to sufficiently deblur any images the microscope with phase mask may take within the predefined DOF 120 in the future.

In some embodiments, a second AI model may be iteratively trained to virtually stain the predicted deblurred image determined by each first AI model 200*a, b*. The second AI model may be or include a cycle generative adversarial network (cycleGAN), unsupervised image-to-image translation (UNIT), or pix2pix. Accordingly, use of a cycleGAN or UNIT may be trained using unpaired training images. That is, the second AI model may be iteratively trained using deblurred training images and stained training images where one deblurred training image does not necessarily correspond to one stained training image. In some embodiments, the focused training images 215*a, b* used to train, in part, the first AI models 200*a, b* may be the deblurred training images used to train, in part, the second AI model. The stained training images may be physically stained by applying a stain to the tissue that the stained training images are of, virtually-stained using any color-space transform known to a person of ordinary skill in the art to mimic a physical stain, or combination thereof. For example, the Beer-Lambert method may be a color-space transform used to mimic a physical hematoxylin and eosin (H&E) stain. In embodiments where both physical and virtual staining are used to generate the stained training images, a two-step training process may be used to train the second AI model as described relative to FIG. 24 below.

Figure 3:
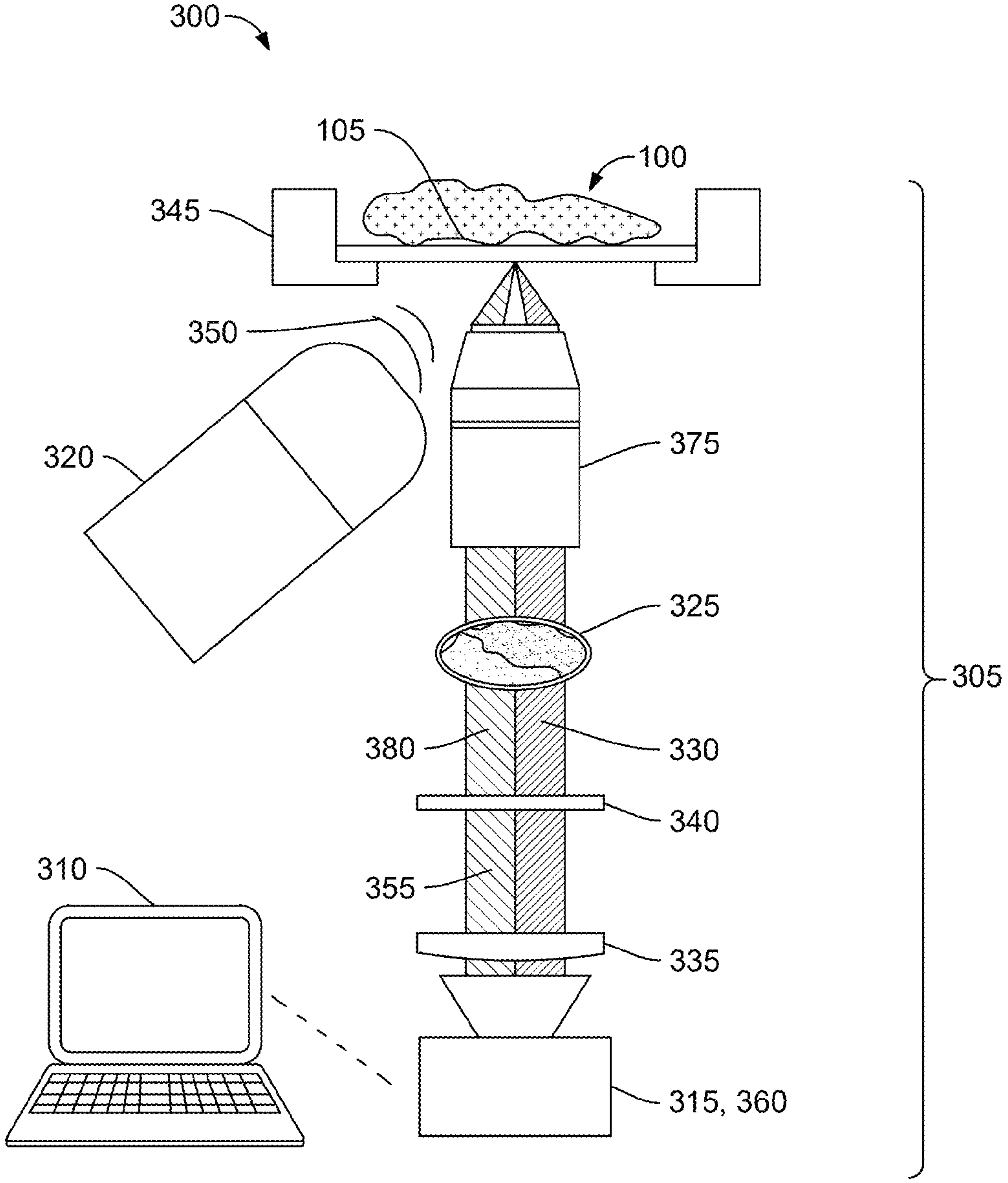
FIG. 3 illustrates a system in accordance with one or more embodiments.

FIG. 3 illustrates the disclosed system 300 in accordance with one or more embodiments. The system 300 includes the microscope 305 and computer system 310 communicably coupled together. The microscope 305 includes a camera 315 and the UV source 320. The microscope 305 further includes the phase mask 325 where the height map 220 of the phase mask 325 is previously determined during the training of one or more first AI models 200*a, b* as described relative to FIG. 2.

The phase mask 325 is disposed within a view 330 of the camera 315. Though FIG. 3 illustrates the phase mask 325 disposed beyond the lens 335 and filter 340 of the camera 315, the phase mask 325 may be disposed further beyond the lens 335 and filter 340 of the camera 315 without departing from the scope of the disclosure.

In some embodiments, the UV source 320 may be disposed adjacent and obliquely to the tissue 100, such as to the side of an objective 375 of the microscope 305. In other embodiments, the UV source 320 may be disposed such that a UV radiation 350 that the UV source 320 emits propagates along a first path 380, such as when using a microscope 305 that does not rely on glass optics as a conventional light microscope relies on. However, a skilled person will appreciate that the UV source 320 may be disposed in any position such that the UV radiation 350 illuminates an imaging area of a stage 345 of the microscope 305 substantially uniformly. FIG. 3 specifically illustrates the tissue 100 as resected tissue. Accordingly, in these embodiments, the resected tissue may be disposed on a stage 345 of the microscope 305. In other embodiments, the tissue 100 is in-vivo tissue. In these embodiments, the microscope 305, in part, may be disposed near or within the in-vivo tissue. To dispose the microscope 305, in part, within the in-vivo tissue, the microscope 305 may include an imaging probe that is communicably coupled to the camera 315. The imaging probe is configured to insert within the in-vivo tissue prior to obtaining an image of the in-vivo tissue.

Returning to FIG. 3, the UV source 320 is configured to emit the UV radiation 350 towards the stage 345 and, thus, the tissue 100. The UV radiation 350 scatters a light 355 illuminating the tissue 100. In doing so, only the surface 105 of the tissue 100 is imaged.

The microscope 305 may include other parts such as, without limitation, a light source 360, condenser (not shown), various filters 340, various lenses 335, various mirrors (not shown), objective 375, and stage 345. The light source 360 is configured to emit the light 355 that propagates along a first path 380 to illuminate the tissue 100. The various filters 340, lenses 335, and mirrors as well as the objective 375 are configured as would be known to a person of ordinary skill in the art. In some embodiments, the stage 345 may be an open-top stage as FIG. 3 illustrates.

Figure 4:
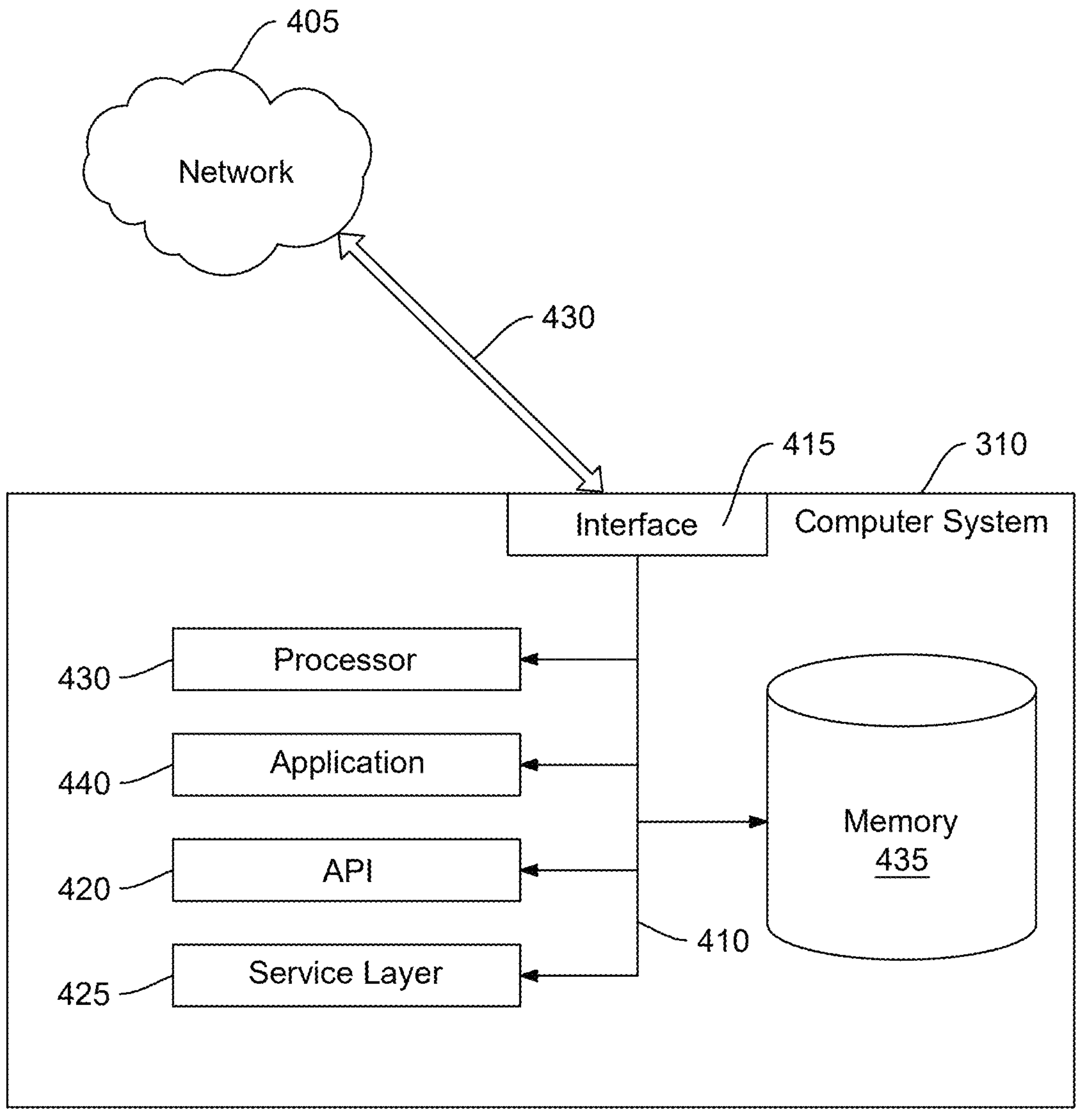
FIG. 4 illustrates a computer system in accordance with one or more embodiments.

FIG. 4 illustrates the computer system 310 of the system 300 in accordance with one or more embodiments. The computer system 310 is intended to depict any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system 310 may include an input device, such as a keypad, keyboard, touch screen, or other device that can accept user information, and an output device that displays information, including digital data, visual or audio information (or a combination of both), or a graphical user interface (GUI). Specifically, the computer system 310 may include a robust graphics card for the detailed rendering of the image, deblurred image, and/or virtually-stained image among other images including further processed images thereof.

The computer system 310 can serve in a role as a client, network component, server, database, or any other component (or a combination of roles) of a computer system 310 as required for image processing. The illustrated computer system 310 is communicably coupled with a network 405. For example, the microscope 305 and computer system 310 may be communicably coupled via the network 405. In some implementations, one or more components of the computer system 310 may be configured to operate within environments, including cloud-computing-based, local, global, or other environment (or a combination of environments).

At a high level, the computer system 310 is an electronic computing device operable to receive, transmit, process, store, and/or manage images, data, and other information associated with the disclosed systems and methods. According to some implementations, the computer system 310 may also include or be communicably coupled with an application server, e-mail server, web server, caching server, streaming data server, business intelligence (BI) server, or other server (or a combination of servers).

The computer system 310 may receive requests over the network 405 from the microscope 305, other computer systems 310, and/or another client application and respond to the received requests by processing the requests appropriately. In addition, requests may also be sent to the computer system 310 from internal users (for example, from a command console or by other appropriate access method), external or third-parties, other automated applications, as well as any other appropriate entities, individuals, systems, or computer systems 310.

Each of the components of the computer system 310 can communicate using a system bus 410. In some implementations, any or all of the components of the computer system 310, both hardware or software (or a combination of hardware and software), may interface with each other or the interface 415 (or a combination of both) over the system bus 410 using an application programming interface (API) 420 or service layer 425 (or combination of the API 420 and service layer 425). The API 420 may include specifications for routines, data structures, and object classes. The API 420 may be either computer-language independent or dependent and refer to a complete interface, single function, or set of APIs 420. The service layer 425 provides software services to the computer system 310 or other components (whether illustrated or not) that are communicably coupled to the computer system 310. The functionality of the computer system 310 may be accessible for all service consumers using this service layer 425. Software services, such as those provided by the service layer 425, provide reusable, defined business functionalities through a defined interface. For example, the interface may be software written in JAVA, C++, LabVIEW, MATLAB, or other suitable language providing data in extensible markup language (XML) format or another suitable format. While illustrated as an integrated component of the computer system 310, alternative implementations may illustrate the API 420 or the service layer 425 as stand-alone components in relation to other components of the computer system 310 or other components (whether or not illustrated) that are communicably coupled to the computer system 310. Moreover, any or all parts of the API 420 or the service layer 425 may be implemented as child or sub-modules of another software module, enterprise application, or hardware module without departing from the scope of this disclosure.

The computer system 310 includes the interface 415. Although illustrated as a single interface 415 in FIG. 4, two or more interfaces 415 may be used according to particular needs, desires, or particular implementations of the computer system 310 and microscope 305. The interface 415 is used by the computer system 310 for communicating with other systems in a distributed environment that are connected to the network 405. Generally, the interface 415 includes logic encoded in software or hardware (or a combination of software and hardware) and operable to communicate with the network 405. More specifically, the interface 415 may include software supporting one or more communication protocols associated with communications such that the network 405 or interface's hardware is operable to communicate physical signals within and outside of the computer system 310.

The computer system 310 includes at least one computer processor 430. Generally, a computer processor 430 executes any instructions, algorithms, methods, functions, processes, flows, and procedures as described above. A computer processor 430 may be a central processing unit (CPU) and/or graphics processing unit (GPU).

The computer system 310 also includes a memory 435 (i.e., a non-transitory computer-readable medium) that stores data and software (i.e., computer-executable instructions) for the computer system 310, microscope 305, or other components (or a combination of both) that can be connected to the network 405. In some embodiments, the memory 435 may store one or more AI models, training images, input images, deblurred images, virtually-stained images, etc. Although illustrated as a single memory 435 in FIG. 4, two or more memories 435 may be used according to particular needs, desires, or implementations of the computer system 310 and microscope 305 and the described functionality. While memory 435 is illustrated as an integral component of the computer system 310, in alternative implementations, memory 435 can be external to the computer system 310.

The application 440 is an algorithmic software engine providing functionality according to particular needs, desires, or implementations of the computer system 310, particularly with respect to functionality described in this disclosure. For example, application 440 can serve as one or more components, modules, applications, etc. Further, although illustrated as a single application 440, the application 440 may be implemented as multiple applications 440 on the computer system 310. In addition, although illustrated as integral to the computer system 310, in alternative implementations, the application 440 can be external to the computer system 310.

There may be any number of computer systems 310 associated with, or external to, the computer system 310 communicably coupled to the microscope 305, where the computer system 310 and microscope 305 communicate over the network 405. Further, the term "client," "user," and other appropriate terminology may be used interchangeably as appropriate without departing from the scope of this disclosure. Moreover, this disclosure contemplates that many users may use the microscope 305 and computer system 310 as a system 300.

Figure 5:
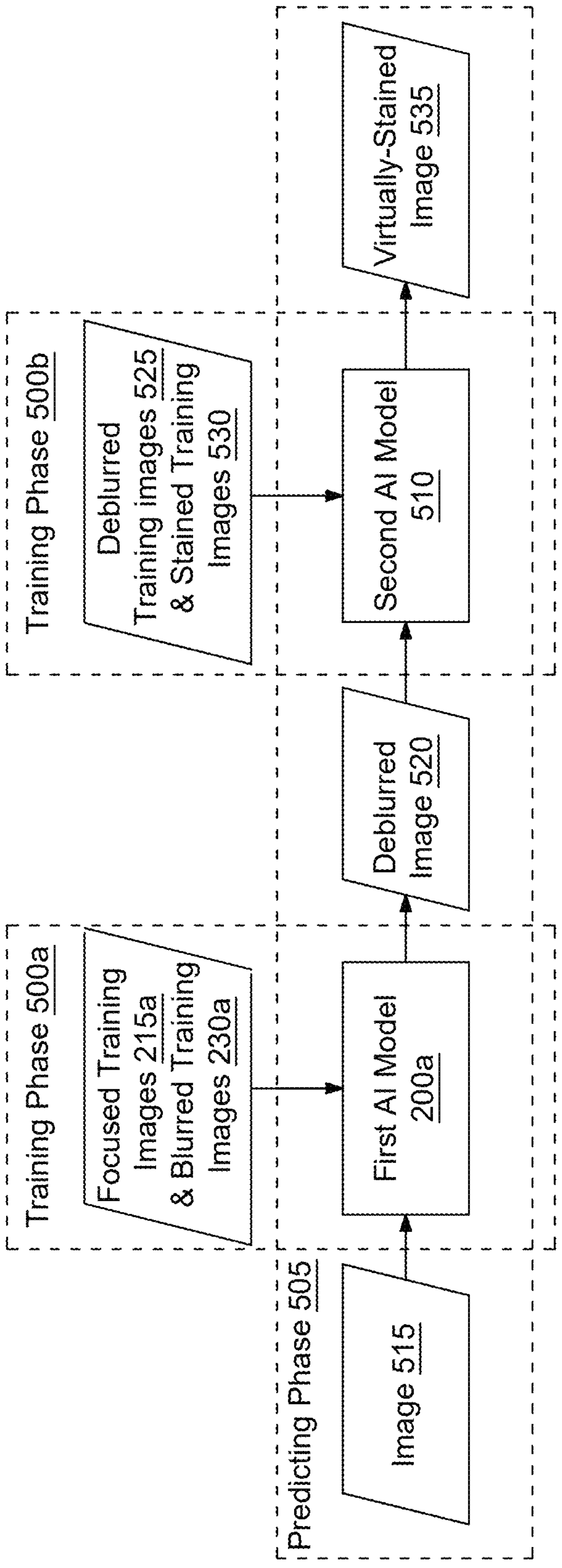
FIG. 5 illustrates training and predicting using first and second AI models in accordance with one or more embodiments.

FIG. 5 illustrates the training phases 500*a, b* and predicting phase 505 of one first AI model 200*a* and second AI model 510 in accordance with one or more embodiments. As previously described relative to FIG. 2, the first AI model 200*a* is trained using focused training images 215*a* and blurred training images 230*a*. Though FIG. 5 only illustrates one first AI model 200*a*, the number of AI models 200*a, b* corresponds to the number of channels of the microscope 305. Accordingly, first AI model 200*a*, focused training images 215*a*, and blurred training images 230*a* shown in FIG. 5 may be replaced with first AI model 200*b*, focused training images 215*b*, and blurred training images 230*b* without departing from the scope of the disclosure.

Following the training phase 500*a* for the first AI model 200*a*, the phase mask 325 is manufactured based on the height map 220. The phase mask 325 is then disposed within the view 330 of the camera 315 of the microscope 305 as illustrated in FIG. 3.

The microscope 305 may be used to obtain an image 515 of the tissue 100. By design of the phase mask 325 and inclusion of the UV source 320 as parts of the microscope 305, the camera 315 obtains the image 515 of the surface 105 of the tissue 100 within the predefined DOF 120. In some embodiments, the microscope 305 may obtain a sequence of images within the predefined DOF 120, each at a unique depth within the predefined DOF 120. This image 515 or sequence of images is less blurry than the image or sequence of images would be if the phase mask 325 and/or UV source 320 were/was not included as a part of the microscope 305. Further, if the microscope 305 is a dual-channel microscope, the image 515 includes a manifestation of features where some features fluoresce at one predefined wavelength 210*a* and some features fluoresce at another predefined wavelength 210*b*. Some of the features and manifestation of features may be diagnostic features.

The image 515 obtained by the microscope 305 is input into trained first AI model 200*a* as illustrated in FIG. 5. In response to the image 515, trained first AI model 200*a* determines or predicts a deblurred image 520. The deblurred image 520 continues to include the manifestation of features where the features fluoresce at predefined wavelength 210*a*. However, the manifestation of features within the deblurred image 520 may be less blurry than they are in the image 515. If the sequence of images is input into the trained first AI model 200*a*, the trained first AI model 200*a* determines or predicts a sequence of deblurred images.

As noted above, the second AI model 510 is trained using deblurred training images 525 and stained training images 530. Following the training phase 500*b*, the deblurred image 520 or sequence of deblurred images is input into the trained second AI model 510. In response to the deblurred image 520, the trained second AI model 510 determines or predicts a virtually-stained image 535. If the sequence of deblurred images is input in the trained second AI model 510, the trained second AI model 510 determined or predicts a sequence of virtually-stained images. The virtually-stained image continues to include the manifestation of features where the features fluoresce at predefined wavelength 210*a*. Some of these manifestations of features may now be virtually-stained.

Figure 6:
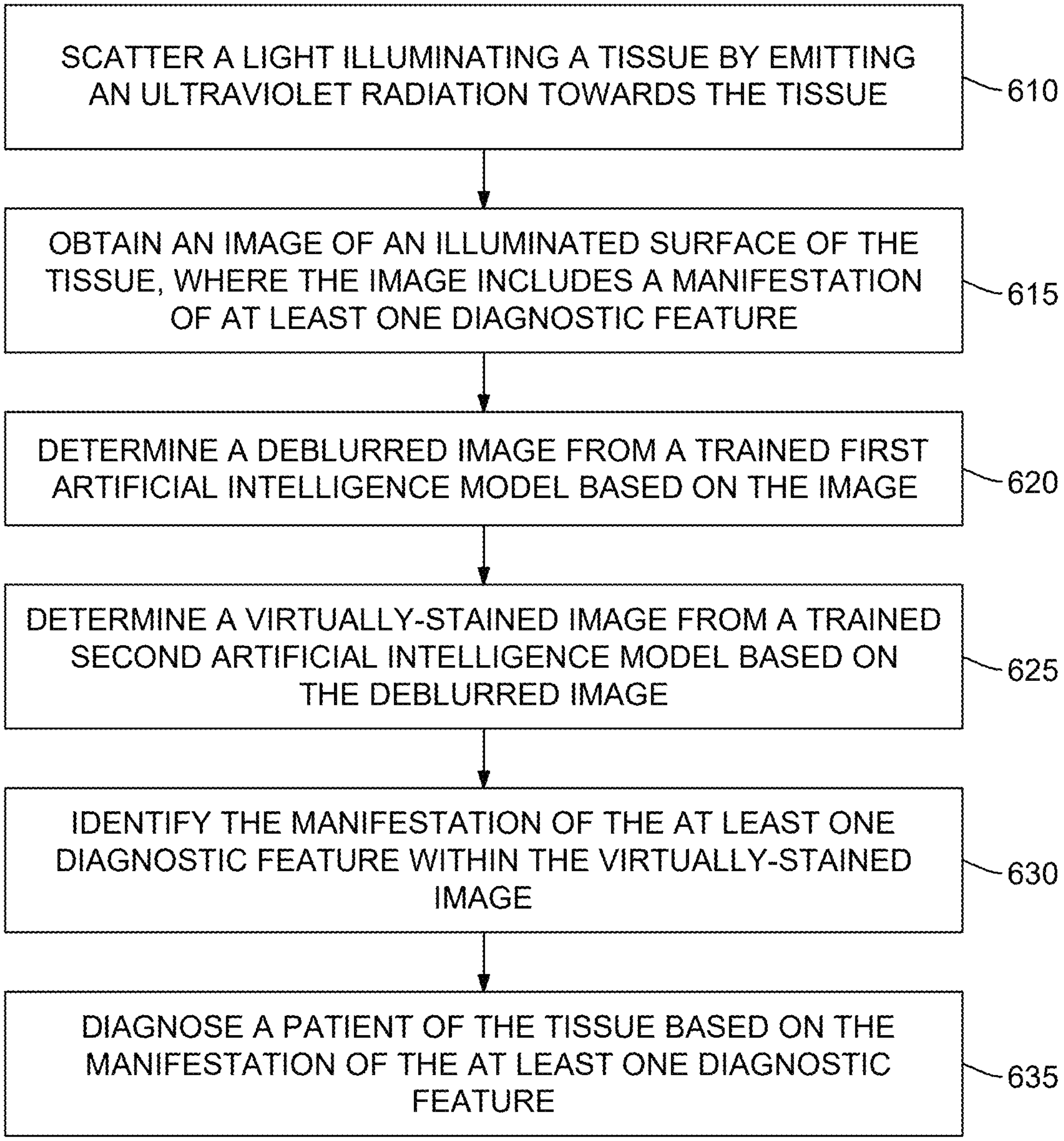
FIG. 6 describes a method in accordance with one or more embodiments.

FIG. 6 describes a method in accordance with one or more embodiments.

In block 610, a light 355 illuminating a tissue 100 is scattered by emitting a UV radiation 350 towards the tissue 100. This is illustrated in FIG. 3. Using the UV radiation 350 to scatter the light 355 limits the intensity of light illuminating the tissue 100 such that only the surface 105 of the tissue is imageable by the microscope 305. The tissue 100 includes at least one diagnostic feature. The diagnostic feature may be any clinically-useful feature or absence of that feature within the tissue 100.

In block 615, an image 515 of an illuminated surface 105 of the tissue 100 is obtained. In some embodiments, the image 515 may be obtained using the disclosed microscope 305 described relative to FIG. 3. The image 515 excludes a nonilluminated portion of the tissue 100. The image 515 is within a predefined DOF 120, inclusive, that the surface 105 of the tissue 100 resides in. The image 515 includes a manifestation of the at least one diagnostic feature. Accordingly, the manifestation may be an absence of the manifestation.

In block 620, a deblurred image 520 of the image 515 is determined using a trained first AI model 200*a*. That is, the image 515 is input into the trained first AI model 200*a* such that the trained first AI model 200*a* determines or predicts the deblurred image 520 in response to the image 515. Accordingly, the deblurred image 520 is more crisp than the image 515.

In block 625, a virtually-stained image 535 of the deblurred image 520 is determined using a trained second AI model 510. That is, the deblurred image 520 is input into the trained second AI model 510 such that the trained second AI model 510 determines or predicts the virtually-stained image 535 in response to the deblurred image 520. The virtually-stained image 535 may be clinically useful and mimic physically-stained images that clinicians routinely use for diagnosis and surgical management. Accordingly, the manifestation of the at least one diagnostic feature may be virtually stained.

In block 630, the manifestation of the at least one diagnostic feature is identified within the virtually-stained image 535. This block may be performed automatically using computer-automated software, manually by a clinician, or a combination thereof.

In block 635, the patient of the tissue 100 is diagnosed based on the manifestation of the at least one diagnostic feature. In the context of this disclosure, "diagnose" may refer to identifying a disease or illness of the patient or identifying whether the diseased tissue or illness is or is not affecting the patient following resection of the tissue 100. For example, in some embodiments, the method may be performed intraoperatively. In these embodiments, diagnosis may refer to whether all diseased tissue has been resected.

Figure 7A:
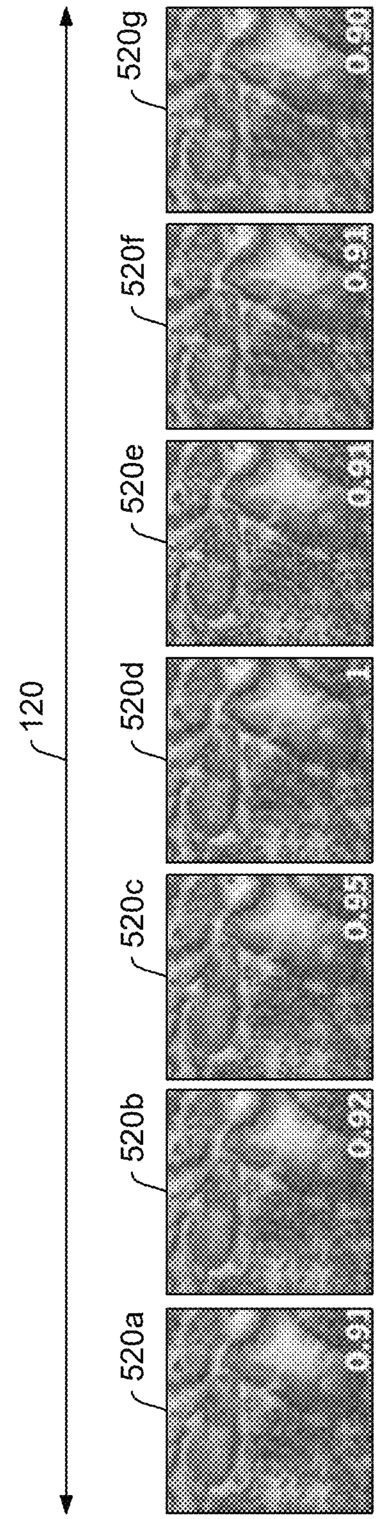
FIG. 7A displays a sequence of deblurred images in accordance with one or more embodiments.

FIG. 7A displays a sequence of deblurred images 520*a-g* in accordance with one or more embodiments. Each lowercase letter among "a" through "g" is associated with a unique depth within the predefined DOF 120. The lowercase letter "a" is associated with the deepest depth within the predefined DOF 120. The lowercase letter "g" is associated with the shallowest depth within the predefined DOF 120. The sequence of deblurred images 520*a-g* is obtained using the disclosed microscope 305 and processed using the first AI model 200*a* to further deblur. Each image among the sequence of deblurred images 520*a-g* is fairly crisp no matter the depth within the predefined DOF 120. The quality of each image among the sequence of deblurred images 520*a-g* is quantified using the Multi-scale Structure Similarity Index Measure (MS-SSIM) where zero indicates poor image quality (e.g., blurry) and one indicates high image quality (e.g., crisp).

Figure 7B:
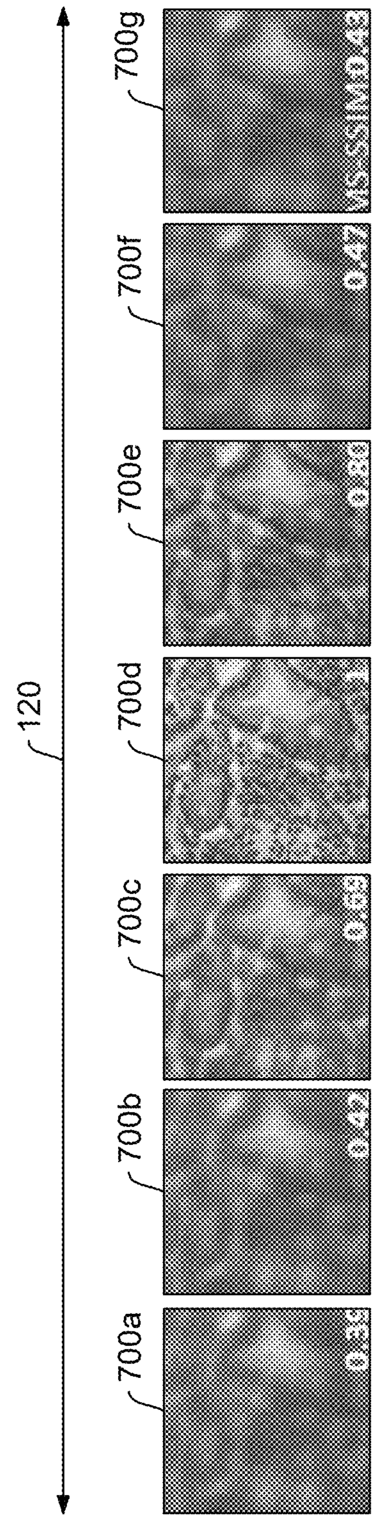
FIG. 7B displays a comparative sequence of images.

FIG. 7B displays a comparative sequence of conventional images 700*a-g*. The comparative sequence of conventional images 700*a-g* is obtained using the conventional microscope and not processed in any way to deblur. Each image among the comparative sequence of conventional images 700*a-g* increases in blurriness as the depth of each image increases away from a central depth (e.g., 0 μm at "d") within the predefined DOF 120.

Upon a comparison of each pair of images where one image is displayed in FIG. 7A and one is displayed in FIG. 7B (e.g., 520*a* versus 700*a*), it can be seen that each of the sequence of deblurred images 520*a-g* in FIG. 7A is more crisp than the corresponding comparative conventional image 700*a-g* as the depth within the predefined DOF 120 either increases or decreases from the central depth within the predefined DOF 120.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

Examples

Histopathology plays a critical role in the diagnosis and surgical management of cancer. However, access to histopathology services, especially frozen section pathology during surgery, is limited in resource-constrained settings because preparing slides from resected tissue is time-consuming, is labor-intensive, and requires expensive infrastructure. The present examples illustrate a deep-learning-enabled microscope, denoted DeepDOF-SE, to rapidly scan intact tissue at cellular resolution without the need for physical sectioning. Three key features jointly make DeepDOF-SE practical. First, tissue specimens are stained directly with inexpensive vital fluorescent dyes and optically sectioned with ultraviolet excitation that localizes fluorescent emission to a thin surface layer. Second, a deep-learning algorithm and phase mask extends the depth-of-field, allowing rapid acquisition of in-focus images from large areas of tissue even when the tissue surface is highly irregular. Finally, a semi-supervised generative adversarial network virtually stains DeepDOF-SE fluorescence images with hematoxylin-and-cosin appearance, facilitating image interpretation by pathologists without significant additional training. The present inventors developed the DeepDOF-SE platform using a data-driven approach and validated its performance by imaging surgical resections of suspected oral tumors. The results show that DeepDOF-SE provides histological information of diagnostic importance, offering a rapid and affordable slide-free histology platform for intraoperative tumor margin assessment in low-resource settings.

Any slide-free approach to real-time histopathology at the point of resection must somehow (a) reduce sub-surface scattering without the need for thin sections, (b) contend with natural surface irregularities without requiring use of a microtome and (c) retain the perceptual appearance of traditional processing to facilitate its integration in the routine clinical practice. The present inventors developed the deep-learning-enabled extended depth-of-field (DOF) microscope with UV surface excitation (DeepDOF-SE) to achieve these goals, by substantially expanding the imaging capability of a simple dual-channel fluorescence microscope with integrated computational and deep learning models. DeepDOF-SE is specifically designed to provide a slide-free histology platform for use in low-resource settings to support immediate biopsy assessment and/or rapid intraoperative assessment of margin status. The 4×, 0.13 NA system can resolve subcellular features needed to diagnose precancer and cancer and is consistent with pathologists' use of 2× and 4× objectives for the vast majority of diagnoses.

In DeepDOF-SE, an aim is to provide histology of tissue surfaces cut with a simple scalpel, where microscopy with UV surface excitation (MUSE) is relied on, which exploits the limited depth of penetration of UV excitation light to limit fluorescent emission only to the tissue surface-thereby limiting the deleterious effects of sub-surface scattering. Thus, UV excitation allows a reduction in sub-surface scattering without the need for thin sections.

In DeepDOF-SE, the microscope depth-of-field is extended by co-designing wavefront encoding and image processing. The end-to-end optics and image processing design in DeepDOF-SE is optimized in two fluorescence channels. These examples demonstrate the capability of DeepDOF-SE to image nuclear and cytoplasmic features simultaneously, and its compatibility with different fluorescence dyes across a broad range of emission wavelengths. Moreover, these examples show that information acquired in two fluorescence channels allows seamless integration of deep-learning-based virtual staining to generate H&E-like histology images.

In DeepDOF-SE, these examples demonstrate a two-step semi-supervised scheme to train the CycleGAN for virtual staining, generating artifact-free virtual H&E while avoiding the need for acquiring paired data. This framework is readily applicable to different staining protocols that provide both nuclear and cytoplasmic feature contrast. Furthermore, these examples report the application of CycleGAN for virtual staining of fresh human oral tumor resections and demonstrate that the present model is capable of visualizing distinct histological features in different layers of oral epithelium.

Figure 8:
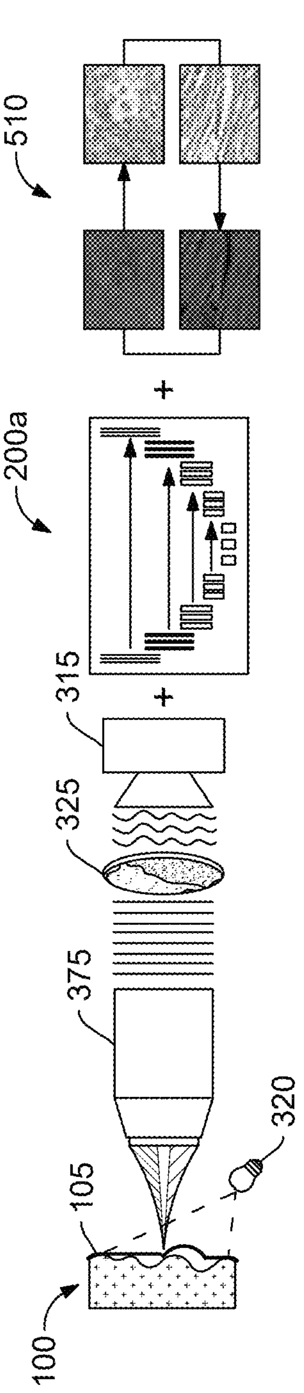
FIG. 8 illustrates a DeepDOF-SE platform.
Figure 9:
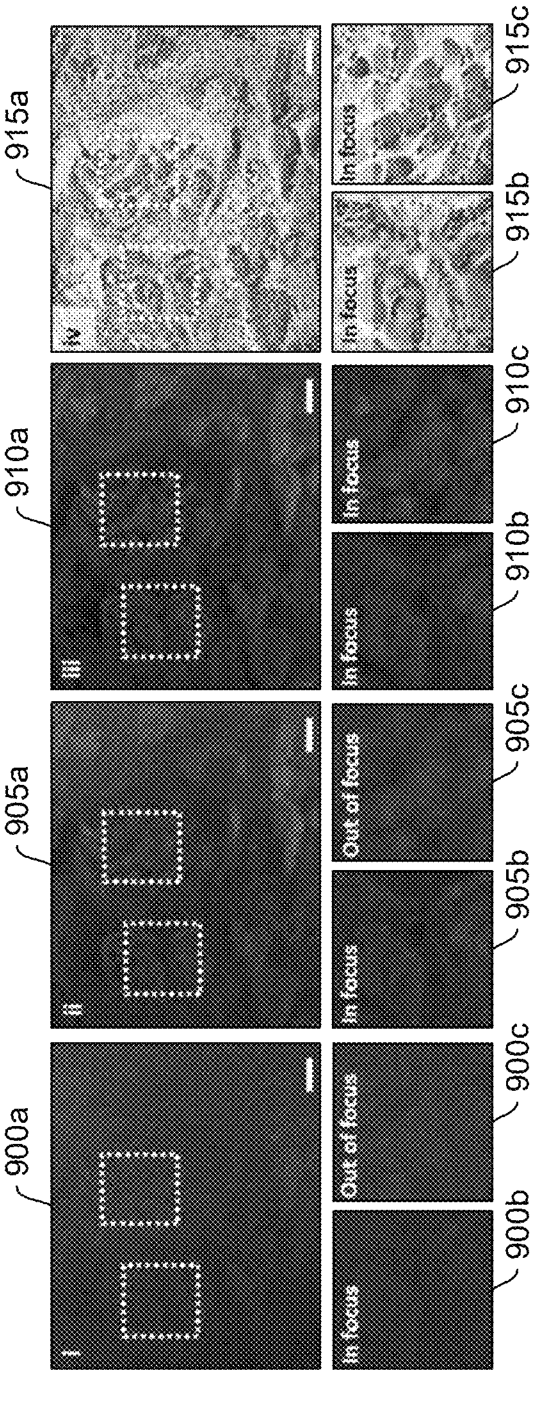
FIG. 9 displays a comparative image (far left), comparative image with ultraviolet (UV) excitation (middle left), deblurred image (middle right), and virtually-stained image (far right).

These examples illustrate the development of DeepDOF-SE by combining surface excitation, extended DOF imaging, and virtual staining by building the DeepDOF-SE based on a simple dual-channel fluorescence microscope and demonstrate its use for rapid histological imaging of fresh intact tissue specimens at a scanning speed of 1.6 $cm^2$/min. These examples incorporate optical sectioning, deep-learning-enabled extended DOF imaging and virtual staining of nuclear and cytoplasmic features to make rapid, cost-effective, and slide-free histology practical. DeepDOF-SE is based on a simple dual-channel fluorescence microscope. Image contrast is provided by briefly immersing fresh tissue samples in a solution containing the vital fluorescent dyes Rhodamine B and DAPI that highlight cytoplasmic and nuclear features, respectively. A jointly-optimized phase mask and reconstruction network (i.e., first AI model 200*a, b*) extend the depth-of-field as shown in FIG. 8, enabling high-resolution images to be collected without refocusing from tissue surfaces that are simply cut with a scalpel. DeepDOF-SE provides the ability to simultaneously acquire images of cytoplasmic and nuclear features in two separate channels. The resulting all-in-focus fluorescence images are virtually stained to resemble H&E-stained sections using a semi-supervised CycleGAN. FIG. 9 demonstrates the improvement in performance provided by surface excitation, extended DOF, and virtual staining. Compared to visible excitation 900*a-c* (dual-channel fluorescence image of porcine specimen stained with Rhodamine B and DAPI), UV excitation suppresses the impact of subsurface scattering 905*a-c*. However, it is challenging to survey a large area (1 $cm^2$ or larger) of scalpel-cut tissue due to surface irregularities that extend beyond the DOF of a conventional microscope, as evidenced by out-of-focus regions of the image 905*a, c*. These examples tackled this challenge by using deep-learning techniques to extend the DOF to 200 μm, consistent with topographic variations in tissue prepared with a simple scalpel, while preserving sub-cellular resolution. As shown in 910*a-c*, the combination of UV excitation and deep-learning extended DOF allows acquisition of an in-focus image from a large area. Finally, 915*a-c* displays the CycleGAN virtual H&E stain of the image, designed to resemble conventional slide-based H&E staining. Using a data-driven and learning-based approach, the examples show that DeepDOF-SE offers a slide-free histology platform suited for rapid histopathologic assessment of fresh tissue specimens that could be performed intraoperatively or in resource-constrained settings as illustrated in Table 1.

TABLE 1

| | Expertise | Time | Infrastructure | Equipment for Sample Preparation | Equipment for Imaging |
|---|---|---|---|---|---|
| Slide-based histology | Trained Histotechnologist | 24 hours (permanent section) 5-10 minutes (frozen section) | Pathology lab | Cryostat Slide stainer | Slide scanner Computer system |
| DeepDOF-SE | Minimal Training | 5-10 minutes | Point of Care | Vital dyes Pilet/scalpel | DeepDOF-SE Computer system |

The DeepDOF-SE fluorescence microscope enables direct in-focus imaging of irregular surfaces of fresh tissue specimens by extending the depth-of-field and leveraging surface excitation. FIG. 2 describes the end-to-end network (i.e., first AI models 200*a, b*) used to jointly design the phase mask and the reconstruction algorithm. The first layer of the end-to-end network uses a physics-informed algorithm to simulate image formation of a fluorescence microscope with the addition of a phase mask. In particular, image formation at two spectral channels that correspond to the vital dyes, Rhodamine B and DAPI, is simulated at 21 discrete depths within the 200 μm DOF. In the following layers of the end-to-end network, two reconstruction U-Nets are used to recover all-in-focus images from the blurred images.

After the network was trained with a dataset containing a broad range of complex features including histologic features, the optimized phase mask design was fabricated and installed in the DeepDOF-SE microscope. FIG. 3 shows the system design based on a simple fluorescence microscope with a standard objective (Olympus Plan Fluorite 4×, 0.13 NA). A UVC LED provides oblique illumination for surface excitation, while the phase mask modulates the wavefront in the optical path to enable the extended depth-of-field imaging. These examples describe performing a one-time calibration of the system by capturing its point spread functions (PSFs) and using the measured PSFs to fine-tune the U-Nets.

Figure 10:
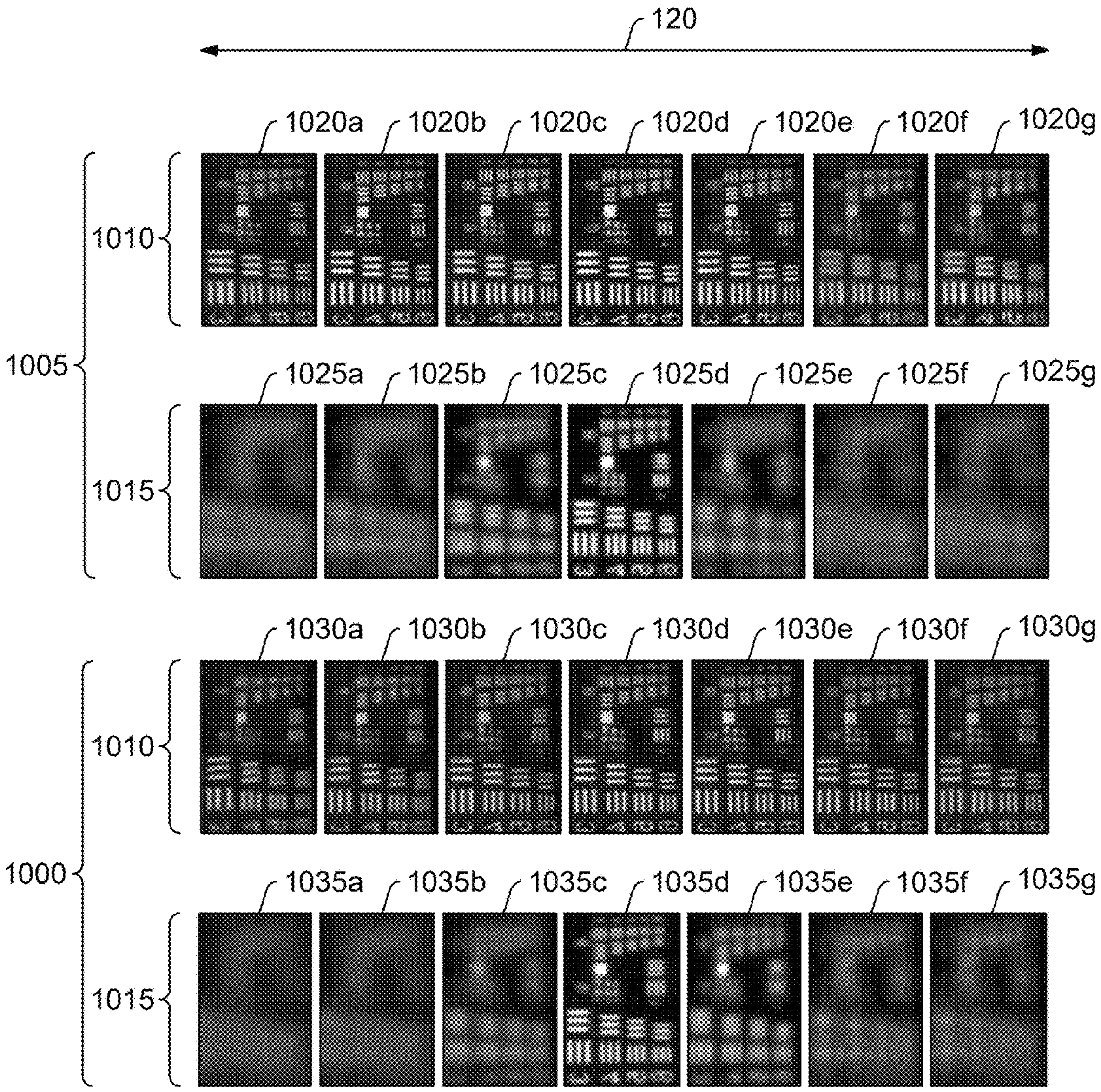
FIG. 10 displays a comparative sequence of images (bottom two rows) and sequence of images (top two rows) for a first channel (top row and middle bottom row) and second channel (middle top row and bottom row).

These examples characterize the spatial resolution of DeepDOF-SE using a negative 1951 USAF resolution target. In FIG. 10, the resolution target was imaged in two fluorescence channels (Rhodamine B 1000 and DAPI 1005) using DeepDOF-SE (i.e., disclosed method 1010 to acquire images (1020*a-g* and 1030*a-g*) and a conventional fluorescence microscope (i.e., conventional method 1015 to acquire images 1025*a-g* and 1035*a-g*) over a sequence of depths a-g within the extended DOF 120. As shown in FIG. 10, significant defocus blur was observed as the USAF target was translated axially through the focal plane of the conventional microscope. In contrast, Group 7 element 5 (2.46 μm line width) is consistently resolved in the Rhodamine B and DAPI fluorescence channels of DeepDOF-SE as the target is translated axially through the target 200 μm depth-of-field. Notably, the present inventors also observed significant axial chromatic aberrations between the two fluorescence channels using the conventional microscope, which can further hinder direct imaging of uneven surfaces. Using the DeepDOF-SE, the chromatic aberrations were significantly reduced due to the extended DOF (see FIG. 20).

The ability of DeepDOF-SE to resolve various clinically-relevant features for samples within the target DOF was evaluated using thin frozen-section tissue slides. The present inventors obtained images of human colon, esophagus, and liver slides that were stained with DAPI and Rhodamine B as slides were translated throughout the target DOF of DeepDOF-SE and compared results to a conventional fluorescence microscope. For better visualization, the present inventors performed a color-space transform using the Beer-Lambert method. FIGS. 7A, 7B, 11A, 11B, 12A, and 12B compare the images taken with DeepDOF-SE and a conventional microscope. DeepDOF-SE consistently resolves varied cellular morphology within the targeted DOF while images acquired with the conventional microscope images suffered from significant blur when the target is out of focus. This observation is corroborated by the Multi-scale Structure Similarity Index Measure (MS-SSIM) score when using the in-focus image as a reference. The MS-SSIM for images acquired with conventional microscopy quickly drops to as low as 0.39 while DeepDOF-SE images maintain a high MS-SSIM (0.85+) across the 200 μm DOF.

Figure 13:
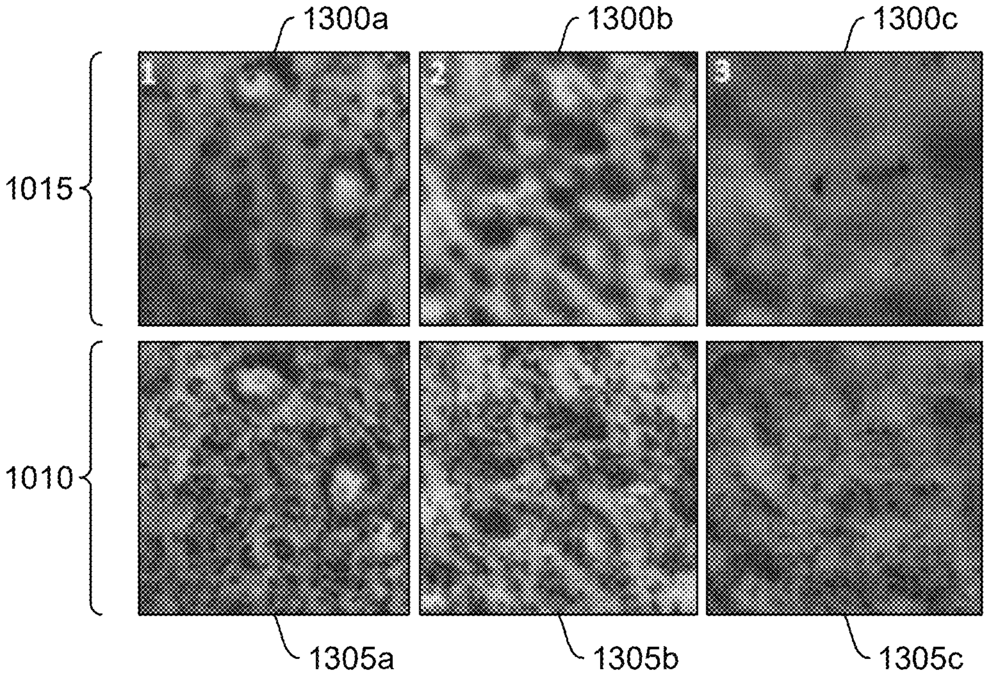
FIG. 13 displays images (bottom row) and comparative images (top row).
Figure 14:
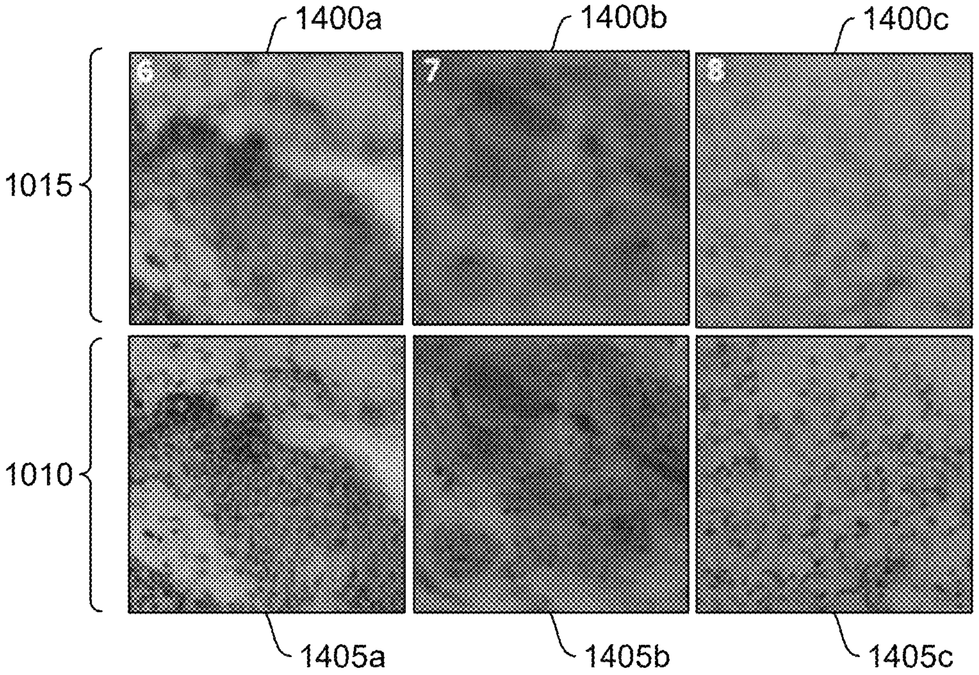
FIG. 14 displays images (bottom row) and comparative images (top row).

The present inventors validated the performance of DeepDOF-SE to image fresh resected tissue specimens and images from a porcine kidney specimen (FIG. 13 shows images 1300*a-c* for the conventional method 1015 and images 1305*a-c* for the disclosed method 1010) and a surgical resection of human oral mucosa (FIG. 14 shows images 1400*a-c* for the conventional method 1015 and images 1405*a-c* for the disclosed method 1010). Specimens were stained with DAPI and Rhodamine B, then imaged with both the conventional microscope and DeepDOF-SE for comparison. The images were virtually stained using Beer-Lambert method for better visualization.

For each sample, ROIs were selected that appeared in focus and out of focus in images (1300*a-c* and 1400*a-c*) collected with the conventional microscope. It was challenging to resolve nuclear features in ROIs that were out-of-focus with the conventional microscope. In contrast, nuclei were clearly resolved in all ROIs of images captured with DeepDOF-SE. Similar subcellular features are present in DeepDOF-SE images and in-focus ROIs imaged with the conventional microscope.

Figure 15:
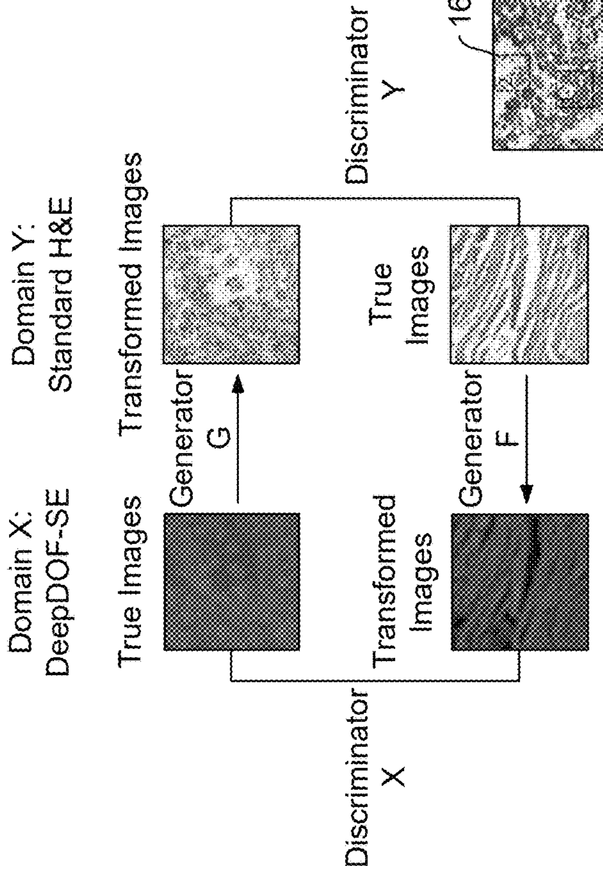
FIG. 15 illustrates the CycleGAN architecture in accordance with one or more embodiments.

The virtual staining of DeepDOF-SE images was modeled as an image-to-image translation that aims to generate images with histology features similar to those in the corresponding standard H&E images. However, it is challenging to acquire image pairs from fresh tissue specimens at the same imaging planes using DeepDOF-SE and standard H&E processing. As a result, the image-to-image mapping network is trained to virtually stain DeepDOF-SE images as part of the CycleGAN architecture (FIG. 15). Unlike deep-learning networks that perform pixel-wise translation, CycleGAN can be effectively trained without paired image sets. As shown in FIG. 15, the two domains X and Y are defined as DeepDOF-SE images and standard H&E images, respectively. The image mapping in each direction is trained using an adversarial architecture; from domain X to Y, for example, the generator G aims to virtually stain DeepDOF-SE images, while the discriminator network $D_Y$ aims to distinguish virtually stained H&E images generated by G from standard H&E images.

Figure 16:
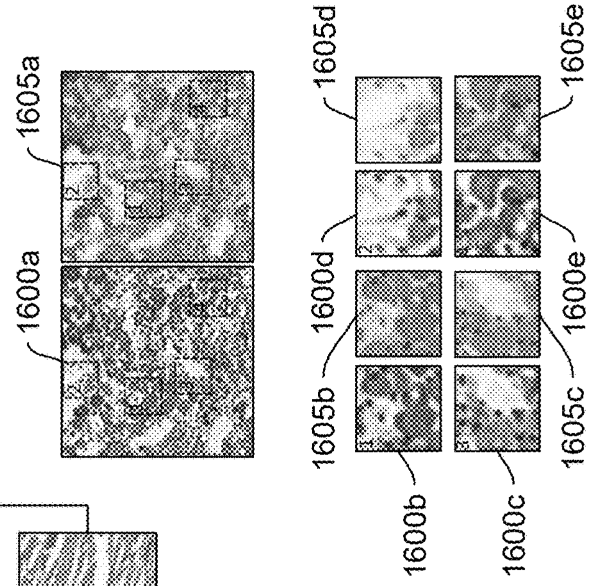
FIG. 16 displays virtually-stained images (top left, left column, and middle right column) and comparative H&E-stained images (top right, middle left column, and right column) for a first field of view.
Figure 17:
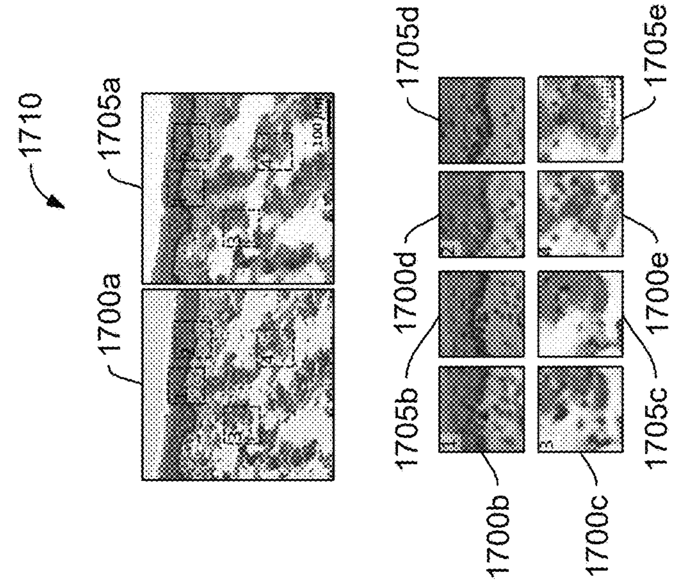
FIG. 17 displays virtually-stained images (top left, left column, and middle right column) and comparative H&E-stained images (top right, middle left column, and right column) for a second field of view.

Since it is known that generative networks can be prone to synthesizing unwanted features, a semi-supervised training procedure was implemented to ensure that both nuclear and cytoplasmic features are accurately translated. FIGS. 16 and 17 and Table 2 validate its ability to preserve clinically-important features. To validate CycleGAN virtual staining, the present inventors used frozen section slides of mouse tongue, which allowed acquisition of co-registered DeepDOF-SE and standard H&E images; the DeepDOF-SE fluorescence images were then virtually stained using the CycleGAN. Automated segmentation algorithms were applied to both the CycleGAN H&E images and the standard H&E images to count the number of nuclei and calculate the average nuclear area (see Table 3 and FIG. 26). Nuclear counts for four selected FOVs are displayed in Table 2. The close agreement between the number of nuclei in CycleGAN stained samples and H&E samples supports the ability of CycleGAN staining to preserve important clinical features. FIGS. 16 and 17 show CycleGAN stained images (1600*a-e* and 1700*a-e*) and H&E stained images (1605*a-e* and 1705*a-e*) of two fields of view (FOV1 1610 and FOV2 1710). In the first FOV 1610 (FIG. 16), cross-sectioned muscle fibers are clearly shown with evenly distributed nuclei in the CycleGAN virtual HE image; similar features are observed in the gold standard H&E image. The second FOV 1710 (FIG. 17) shows the epithelium with underlying lamina propria and muscle fibers; the layered epithelial cell structure and the basement membrane are clearly shown in the CycleGAN virtual H&E image. Importantly, when compared to the gold standard H&E images, the CycleGAN virtual H&E images show co-localized nuclei and cytoplasmic features across the entire FOV, confirming that the CycleGAN performs virtual staining while accurately preserving clinically-important features. The present inventors observed minor color differences between the CycleGAN virtual H&E and standard H&E images, which can be attributed to the known color variations during standard H&E processing.

TABLE 2

| | CycleCAN H&E | Standard H&E |
|---|---|---|
| FOV1 | 465 | 466 |
| FOV2 | 433 | 426 |
| FOV3 | 548 | 567 |
| FOV4 | 431 | 448 |

TABLE 3

| | Nuclear Count | | | Mean Nuclear Area ($\mu m^2$) | | |
|---|---|---|---|---|---|---|
| | Beer-Lambert | CycleGAN H&E | Standard H&E | Beer-Lambert | CycleGAN H&E | Standard H&E |
| FOV1 | 471 | 465 | 466 | 40.40 | 31.93 | 27.84 |
| FOV2 | 424 | 433 | 426 | 36.02 | 31.00 | 28.11 |
| FOV3 | 510 | 548 | 567 | 39.60 | 37.27 | 35.35 |
| FOV4 | 448 | 432 | 448 | 34.31 | 31.83 | 28.36 |

Figure 18:
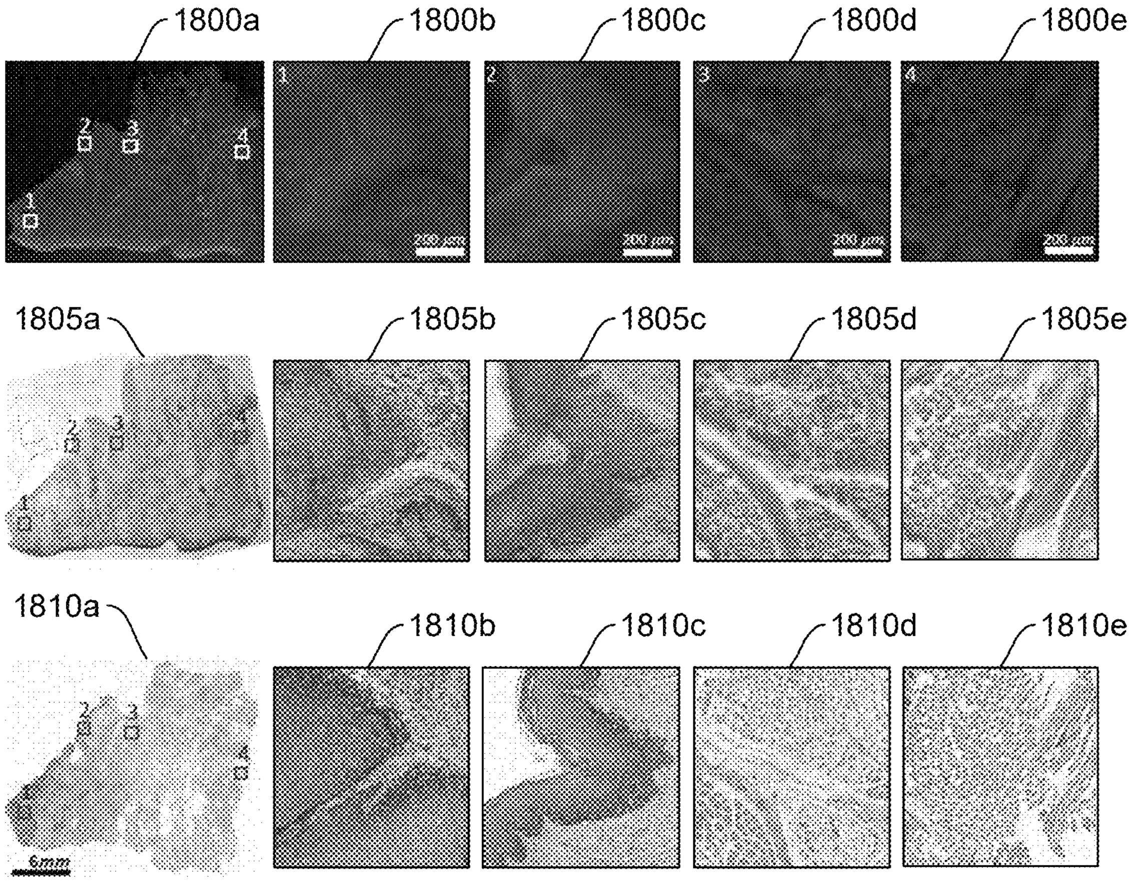
FIG. 18 displays images (top row), virtually-stained images (middle row), and comparative H&E-stained images (bottom row).
Figure 19:
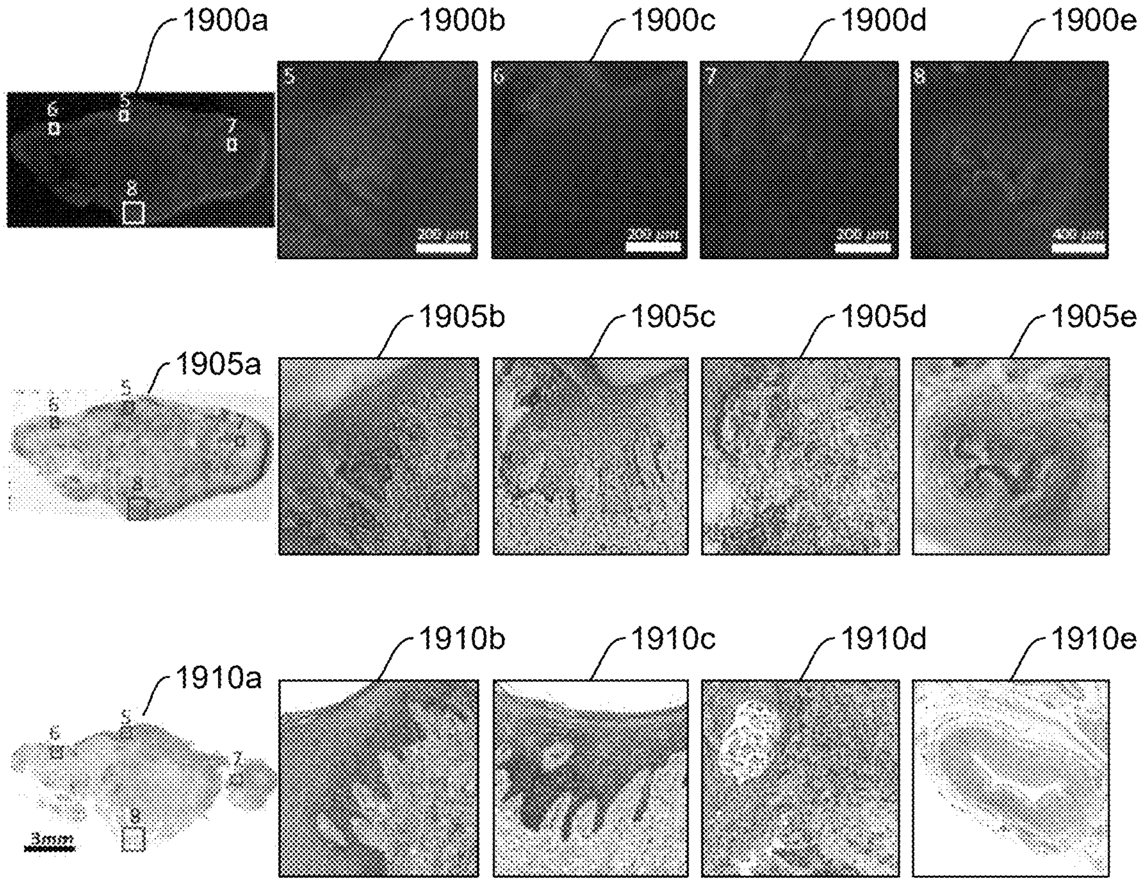
FIG. 19 displays images (top row), virtually-stained images (middle row), and comparative H&E-stained images (bottom row).

The diagnostic potential of the DeepDOF-SE microscope was assessed by comparing DeepDOF-SE images of freshly resected tissue virtually stained using CycleGAN to the gold-standard formalin fixed paraffin embedded (FFPE) H&E scan of the same tissue. FIGS. 18 and 19 show images of two large specimens from freshly resected head and neck squamous cell carcinoma. Each specimen was transected with a scalpel; fluorescence images (1800*a-e* and 1900*a-e*), virtually-stained images (1805*a-e* and 1905*a-e*) using the CycleGAN from the DeepDOF-SE, and physically-stained images (1810*a-e* and 1910*a-e*) are displayed in FIGS. 18 and 19. Subsequently, FFPE H&E sections were prepared from the same samples (FIG. 19). Representative ROIs from these specimens reveal various histopathologic features in different tissue types and disease status; importantly, matching cellular details between the DeepDOF-SE GAN staining images and FFPE H&E images are observed in these ROIs. The present inventors observed subtle color differences between CycleGAN virtual staining and standard H&E staining. These differences are quite similar to variations in the intensity of staining that occur from lab to lab and daily within a single lab. Variations in factors such as the age of stains or the precise staining time can lead to intensity variations and overstaining issues in H&E-stained slides. Despite these differences, epithelial architecture and cellular detail are clearly discerned in both, providing sufficient diagnostic information for clinical evaluation.

Four selected FOVs from the surface epithelium with underlying connective tissue and skeletal muscle bundles are shown across each of the cross-sectioned specimens in FIGS. 18 and 19. In the stratified squamous epithelial layers, ROIs 1, 2, 5, 6 show the individual nuclei with clearly visible basal layer with attached basement membranes. Specifically, ROI 1 shows hyperplasia with dysplasia, while ROIs 2, 5, and 6 display hyperkeratosis, evidenced by the increased thickness of the surface keratin. Invasive islands of squamous cell carcinoma characterized by cellular and nuclear atypia and dyskeratosis were noted within the connective tissue underlying the surface epithelium in ROI 7. ROIs 3 and 4 show skeletal muscle bundles below the lamina propria that are sectioned in cross- and longitudinal-directions found in the H&E section were also observed in the DeepDOF-SE images. A large muscular artery that was noted within submucosa of H&E-stained section can be also identified in the DeepDOF-SE image in ROI 8. These findings were confirmed by the study pathologist (N.V) through standard histopathology evaluation.

Optically sectioned, high resolution and extended depth-of-field imaging of intact tissue sample images were obtained using DeepDOF-SE, a platform designed using a data-driven approach for slide-free histology. Exemplary components of DeepDOF-SE, including deep UV excitation, end-to-end designed extended DOF, and cycleGAN-based virtual staining, jointly enable rapid and slide-free histological examination of fresh tissue specimens with highly irregular surfaces. The DeepDOF-SE images reveal a broad range of diagnostic microscopic features within large areas of tissue cross sections. Moreover, varied types of histological architecture in benign and neoplastic conditions are clearly visualized in the CycleGAN virtually stained H&E images, and histologic findings based on DecpDOF-SE images are confirmed by the gold standard H&E histopathology.

Unlike conventional histopathology that is time-consuming and requires expensive equipment, the DeepDOF-SE platform is low-cost to build (reducing the cost by around 95%), requires minimal training to use, and takes less than 10 minutes to stain and image a 7 $cm^2$ tissue sample (4 min for tissue staining and <5 min for tissue scanning). Compared to conventional pathology requiring mechanical sectioning using a microtome, the present inventors employ a simple yet effective optical sectioning approach via deep UV excitation. Conventional histopathologic diagnosis is based on H&E stained tissue sections and hence, pathologists are accustomed to interpreting H&E stained tissue sections. Using DAPI as the nuclear stain and Rhodamine B as the counter stain, DeepDOF-SE can image cell nuclei and cytoplasmic features. The present inventors apply the deep-learning-based CycleGAN to virtually stain the all-in-focus fluorescence images. The resulting virtual H&E images revealed diagnostic histopathology matching the corresponding standard slide-based H&E images. While it is challenging to achieve serial sectioning with DeepDOF-SE in cases where diagnosis on the surface is equivocal, it is possible to rapidly scan the opposite side of a 4 mm tissue slice using DeepDOF-SE. Alternatively, the slice can be further cut with a scalpel in 2-3 mm steps before scanning again. DeepDOF-SE leverages a simple optical modulation element with deep learning to substantially augment the performance of a fluorescence microscope for high-throughput, single-shot histology imaging. As a result, the DeepDOF-SE platform can be readily built using a modular design approach at a low cost; all of its key components, including the external deep UV LED, the phase mask, the fluorescence filter, the sample stage and computing hardware, can be seamlessly integrated into a simple microscope system with minimal optical and hardware modification. Moreover, the fast and slide-free tissue preparation requires minimal training and does not interrupt standard-of-care procedures, making the technology suitable for broad dissemination in resource-constrained settings. The present initial clinical assessment of DeepDOF-SE demonstrates its capability to rapidly provide histological information of fresh surgical specimens (as shown in FIGS. 18 and 19), including those needed for the diagnosis of precancer and cancer, such as architectural abnormalities, pleomorphism, and abnormal nuclear morphology and increased nuclear-to-cytoplasmic ratio. In cases where a higher resolution is desired, the present approach can serve as a rapid triage tool to identify suspicious regions for further examination at a higher magnification. Based on the results, in a larger study, using standard H&E as a baseline, the present inventors expect to establish diagnostic criteria based on DeepDOF-SE images, and refine the criteria since it was previously shown that nuclear count in optically sectioned fluorescence images using 280 nm excitation is slightly elevated than conventional H&E. To facilitate its evaluation in a clinical setting, the present inventors will enclose the system in a compact housing. In addition, the imaging throughput will be further improved by incorporating a high-sensitivity sensor, higher levels of illumination and faster sample scanning motors.

The DeepDOF-SE platform leveraged two deep learning networks in its system design and data processing pipeline, and employed different training strategies based on the nature of their tasks. The end-to-end extended DOF network aims to simulate physics-informed image formation and reconstruction that are insensitive to image content, and therefore, a data-agnostic approach was used for training. In contrast, since the CycleGAN virtual staining network is designed to perform domain-wise image translation, the training and validation scope were confined using images from the tongue in the current study. Specifically, in the extended DOF network, an eclectic training dataset was used, where the eclectic training set contained various features ranging from multiple types of FFPE H&E images to natural scenes; during validation and testing, fluorescence images of different tissue types are reconstructed. This variability can help the model become more robust and adaptable to different types of inputs during inference, allowing it to generalize to a wider range of applications. The cycleGAN was trained and validated with images from oral tissue surgeries in a clinical study and frozen slides of mouse tongue. While it faithfully translates the DeepDOF-SE fluorescence images of oral tissue to standard H&E appearance, further data collection and clinical evaluation are needed to extend the GAN-based virtual staining to other tissue types. Adipose cells appear intact in DeepDOF-SE images of fresh tissue, while they show a network of thin cell membranes with clear lumens in standard H&E. This is expected since the cytoplasmic lipids within the adipocytes are removed during tissue dehydration using different concentrations of alcohol.

In conclusion, these examples illustrate a deep-learning enabled DeepDOF-SE platform that enhanced the ability of conventional microscopy to image intact, fresh tissue specimens without the need for extensive sample preparation. The deep-learning enabled DeepDOF-SE platform performance was validated to provide diagnostic information in oral surgical resections as confirmed by standard slide-based histopathology. As a fast, easy-to-use, and inexpensive alternative to standard histopathology, the present inventors believe the DeepDOF-SE is useful clinically, especially for intraoperative tumor-margin assessment and for use in under-resourced areas that lack access to standard or frozen section histopathology.

The research for the present examples involved an ex vivo protocol where consenting patients undergoing surgery for oral cancer resection were enrolled at the University of Texas MD Anderson Cancer Center. The study to obtain the results described in these examples was approved by the Institutional Review Boards at the University of Texas MD Anderson Cancer Center and Rice University.

As shown in FIG. 3, The DeepDOF-SE microscope is built using a dual-channel fluorescence microscope with UV surface excitation and the addition of a deep-learning optimized phase mask. The UV LED (Thorlabs M275L4), coupled with a condenser and focusing lens, is pointed at an oblique angle to the sapphire sample window (KnightOptical, WHF5053), illuminating the sample uniformly from beneath. Fluorescence emission from the vital-dye-stained tissue sample is collected by an Olympus 4× objective (RMS4x-PF, 0.13 NA), modulated by the phase mask, and then an image is relayed by a f150 mm tube lens (Thorlabs AC254-150-A) onto a 20-megapixel color CMOS camera (Tucsen FL20). A dual-bandpass filter (Chroma 59003m, 460/630 nm) is used for collecting fluorescence from the Rhodamine B and DAPI channels simultaneously.

For convenient placement of large surgical specimens, the DeepDOF-SE has an open-top sample stage with a circular imaging window 50 mm in diameter. Rapid scanning is enabled by two motorized linear stages (Zaber X-LHM100A). With the designed 3.3× magnification, the FL20 camera provides a 3.9×2.6 $mm^2$ field-of-view per frame. To ensure sufficient overlap between frames for field of view stitching, 2 mm was chosen for stage step motion and scanned 40 frames per minute. The scanning process is controlled and automated using a custom LabVIEW GUI. Briefly, using the GUI, the scanning region is first defined with user input, and images are then acquired and saved sequentially using scanning coordinates automatically calculated based on the scanning range and stage step size.

In this work, an architecture was employed to enable EDOF imaging in a dual-channel fluorescence microscope. Overall, the end-to-end network consists of an optical layer to optimize the imaging optics and a digital layer to optimize the image reconstruction.

The first layer of the end-to-end extended DOF network parameterizes the design of a phase mask and simulates image formation of a dual-channel fluorescence microscope from the specimen to the sensor, with its wavefront at the pupil plane modulated by the phase mask. In these examples, the deep learning network was designed for two fluorescence channels centered at 473 nm and 640 nm, corresponding to emission of DAPI and Rhodamine B, respectively.

The image formation is simulated based on Fourier optics. Briefly, in each fluorescence channel, an image $I_\lambda(x_2, y_2)$ formed by the microscope is the result of scene $I_0(x, y)$ convolved with the point spread function (PSF) at the given wavelength λ summed across depth z.

$$I_\lambda(x_2, y_2) = \sum_z I_0(x, y; z) \otimes PSF_\lambda(x_2, y_2; z) \tag{1}$$

The PSF is the squared magnitude of the Fourier transform of the pupil function $P_\lambda(x_1, y_1; z)$ $$PSF_\lambda(x_2, y_2; z) = \left|\mathcal{F}\{P_{\lambda(x_1, x_2; z)}\}\right|^2 \tag{2}$$

With the amplitude of the pupil function fixed, the phase component of the pupil function (Φ) encodes the defocus blur $\Phi^{DF}$ and the depth-independent mask modulation $\Phi^M$.

$$\Phi_\lambda(x_1, y_1; z) = \Phi_\lambda^{DF}(x_1, y_1; z) + \Phi_\lambda^M(x_1, y_1) \tag{3}$$

In the equation above, the mask modulation term $\Phi^M$ is modulated by the height map of the phase mask, which is parameterized using the first 55 Zernike basis in the first layer of the end-to-end optimization network. In addition, the defocus phase is modeled as $$\Phi_\lambda^{DF}(x_1, y_1; z) = \frac{2\pi}{\lambda} W_m \frac{x_1^2 + x_2^2}{R^2} \tag{4}$$

where R is the radius of the pupil and $$W_m = \frac{R^2}{2} * \frac{(z_0 - z)}{z_0^2}$$

is the maximum path-length error at the edge of the pupil due to defocus where z and $z_0$ are the defocused imaging depth and in-focus depth respectively.

For a given scene, the final sensor image was simulated from two wavelengths corresponding to the two fluorescence channels, and 21 discrete depths evenly discretized in the targeted DOF range of 200 μm. This corresponds to $$\frac{2\pi}{\lambda}$$

$W_m$ ranges of [−8.73, +8.73] at 473 nm and [−11.88, +11.88] at 640 nm. The sensor noise was approximated by adding a Gaussian read noise with a standard deviation of 0.01 in the range of [0, 1].

Sensor images from different defocus in two fluorescence channels are further processed using the image reconstruction layers to recover in-focus images of the specimen. As shown in FIG. 2, the digital layer consists of two deep neural networks of a U-Net architecture.

To ensure the system is capable of imaging a wide variety of features, the network was trained with a large dataset that contains a broad range of imaging features. Specifically, the dataset contains 600 high resolution proflavine-stained oral cancer resections, 600 histopathology images from Cancer Genome Atlas Center FFPE slides, and 600 natural images from the IRNIA holiday dataset (each 1000×1000 pixels, gray scale). While these images have diverse features, they are all in gray scale and cannot be directly used to train DeepDOF-SE, which generates color images. Natural RGB images are also not suitable because the color images captured by fluorescence microscopes contain different information in each color channel. Instead of collecting a new color dataset, which is costly and time-consuming, two different images were randomly combined from the DeepDOF dataset for the DAPI channel and the Rhodamine B channel as input during training; this provides effective training while eliminating cross-talks between the two fluorescence channels.

The 1800 images in the DeepDOF dataset were randomly separated into training, validation, and testing sets. To increase data variability, the images were augmented with random cropping (from 256×256 to 326×326 pixels), rotation, flipping, and brightness adjustment. Since the dataset contains a rich library of features including both histopathological and other features in nature scenes, it is broadly applicable to training image reconstruction pipelines using different microscope objectives with proper rescaling.

The network was implemented using the TensorFlow package and optimized using Adam. The learning rate was chosen empirically at 1e-9 for the optical layer and 1e-4 for the digital layer. The network was trained in two steps. In the first step, the optical layer was fixed to be the cubic mask and only trained the U-Net. In the second step, the optical and digital layer were jointly trained. For both steps, convergence occurred at around 30,000-40,000 iterations.

To account for the difference between the simulated PSF and the experimental PSF during system implementation, a one-time calibration was performed. A monolayer of 1 μm fluorescent beads (Invitrogen T7282, TetraSpeck microspheres, diluted to 105/mL) was imaged as a calibration target, and the right-angle mirror was adjusted behind the objective and a micrometer tilt stage (#66-551, Edmund Optics) installed on the sample stage to achieve uniform focus across the sample imaging window.

To capture the PSFs in the two fluorescence channels, fluorescent TetraSpeck beads were used, where the beads were stained with four fluorescent dyes at 360/430 nm (blue), 505/515 nm (green), 560/580 nm (orange) and 660/680 nm (dark red). The beads were illuminated using a 365 nm LED (Thorlabs M365LP1) for better excitation, and PSFs were measured at 31 depths at 10 μm intervals. At each depth, temporal averaging over five frames and background subtraction was performed to reduce noise.

Twenty-one depths were selected for the target DOF for network fine-tuning. When retraining the network, the optical layer was fixed and the experimentally captured PSF was used to fine-tune the network.

The resolution of DeepDOF-SE was characterized by imaging a US Air Force 1951 resolution target with an added fluorescent background. Illumination was provided by a 405 nm LED. Frame averaging and background subtraction were performed to enhance the signal-to-noise ratio.

Fresh surgical cancer resections from the oral cavity were imaged to evaluate the imaging performance of DeepDOF-SE. In the present ex vivo protocol, consenting patients undergoing surgery for oral cancer resection were enrolled. The excised specimen was first assessed by an expert pathologist and sliced into 3-4 mm thick slices with a standard scalpel. Selected slices were processed for standard frozen-section pathology. The remaining slices were cleaned with phosphate buffered saline (PBS, Sigma-Aldrich P4417, pH 7.2-7.6, isotonic) to remove residuals such as mucus and blood, stained with DAPI (Sigma-Aldrich MBD0015, diluted with PBS, 500 ug/mL) for 2 minutes and Rhodamine B (Sigma-Aldrich 83689, dissolved in PBS, 500 ug/mL) for 2 minutes, and excessive stain was rinsed off with PBS. The tissue was then imaged using the DeepDOF-SE microscope. The raw frames were processed with the DeepDOF-SE networks and stitched using Image Composite Editor (Microsoft, discontinued and other stitching software can be applicable). Post-imaging, the specimens were processed through FFPE histopathology at University of Texas MD Anderson Cancer Center, and the slides were imaged using a slide scanner to provide the standard H&E images. The study was approved by the Institutional Review Boards at the University of Texas MD Anderson Cancer Center and Rice University.

Freshly resected ex-vivo porcine samples were obtained from an abattoir. The tissue was cut with a scalpel, cleaned with PBS to remove residuals such as mucus and blood, and then stained with DAPI (500 ug/mL) for 2 minutes and Rhodamine B (500 ug/mL) for 2 minutes. Excessive stain was rinsed off with PBS, and the tissue was imaged using DeepDOF-SE and a conventional MUSE microscope with the same standard objective.

Frozen-section tissue slides (Zyagen, Inc) were fixed in buffered acetone (60% v/v) for 20 minutes and rinsed in PBS twice for five minutes each. Slides were then stained with DAPI (500 ug/mL) for 2 minutes and Rhodamine B (500 ug/mL) for 2 minutes, and excessive stain was rinsed off with PBS. The stained slide was imaged with DeepDOF-SE without a coverslip on the sapphire window, with the tissue side facing downward. Since glass slides have autofluorescence, the background signal was subtracted before any downstream processing. For the cycleGAN validation study, the imaged frozen section slides were sent to University of Texas MD Anderson Cancer Center for standard H&E staining.

In this study, no statistical method was used to predetermine sample size. For FIGS. 6, 11, 12, 13, and 14 of the main text, the samples are imaged once with the proposed DeepDOF-SE and once with the conventional baseline. For FIGS. 16, 17, 18, and 19, the samples are imaged once with the proposed DeepDOF-SE.

A Beer-Lambert-law-based method was used to assist visualization of DeepDOF-SE images in a color space similar to H&E staining; since it is an analytical method, it preserves both in- and out-of-focus features in DeepDOF-SE images. In this virtual staining method, the transmission T of a wavelength λ through a specimen containing N absorbing dyes can be represented as $$T_\lambda = \exp\left(-\sum_{i=1}^{N} \sigma_{\lambda,i} c_i\right) \quad (5)$$

Where $\sigma_{\lambda,i}$ is the wavelength-dependent attenuation for the i-th dye and $c_i$ is the thickness integrated concentration of the i-th dye per area on the slide. In the case of a digital image, the transmission $T_M$ of M-th color channel can be written as $$T_M = \exp\left(-\sum_{i=1}^{N} \beta_{M,i} I_i k\right) \quad (6)$$

Where $\beta_{M,i}$ is the attenuation of the i-th dye integrated over the spectral range of the M-th channel, $I_i$ is the intensity image for i-th dye, and k is an arbitrary scaling constant that accounts for detector sensitivity etc. In the case of mapping to H&E staining in RGB space, the expression for each channel is as follows:

$$R = \exp(-\beta_{hematoxylin,red} I_{nuclei\ stain} k)\exp(-\beta_{eosin,red} I_{counter\ stain} k) \quad (7)$$

$$G = \exp(-\beta_{hematoxylin,green} I_{nuclei\ stain} k)\exp(-\beta_{eosin,green} I_{counter\ stain} k) \quad (8)$$

$$B = \exp(-\beta_{hematoxylin,blue} I_{nuclei,stain} k)\exp(-\beta_{eosin,blue} I_{counter\ stain} k) \quad (9)$$

The scaling constant k was empirically chosen to be 2.5 for images of range [0, 255], $\beta_{eosin,red}=0.05$, $\beta_{hematoxylin,red}=0.86$, $\beta_{eosin,green}=1.00$, $\beta_{hematoxylin,green}=1.00$, $\beta_{eosin,blue}=0.544$, and $\beta_{hematoxylin,blue}=0.30$.

The domain-wise image translation from DeepDOF-SE images (domain X) to standard H&E images (domain Y) was trained using CycleGAN, a network architecture capable of unpaired image-to-image translation. Briefly, the network consists of two generators, G that maps DeepDOF-SE images (X) to H&E images (Y) and F that maps H&E images (Y) to DeepDOF-SE images (X). For each generator, a discriminator network is tasked to distinguish images synthesized by the generators from the ground truth image set ($D_X$ for F and $D_Y$ for G). The generator networks are 9-block ResNets and the discriminator networks are 70×70 PatchGANs; instance normalization is implemented in all networks.

Figure 24:
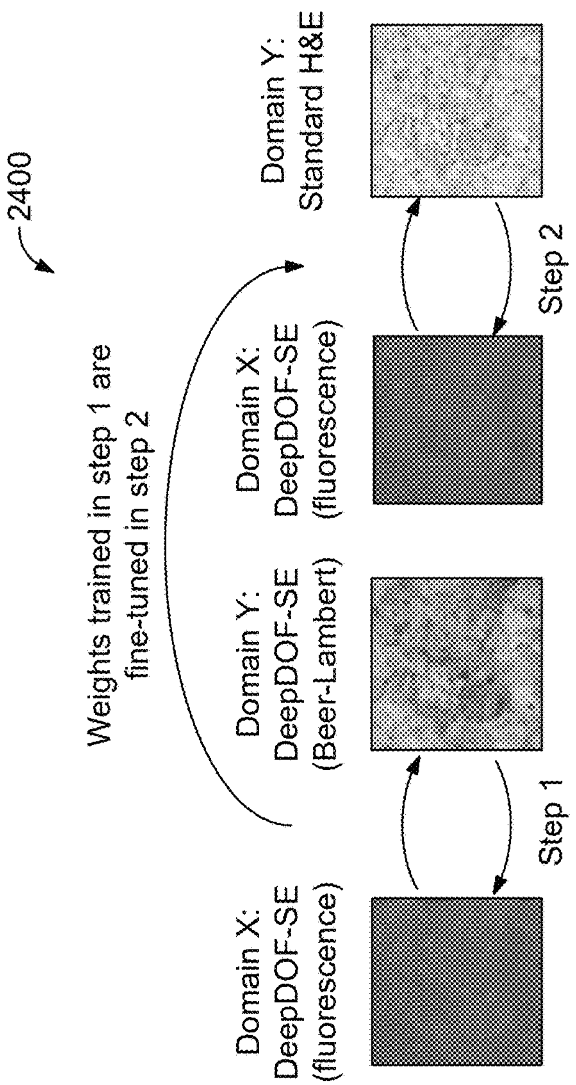
FIG. 24 shows a two-step training scheme for the second AI model.
Figure 23:
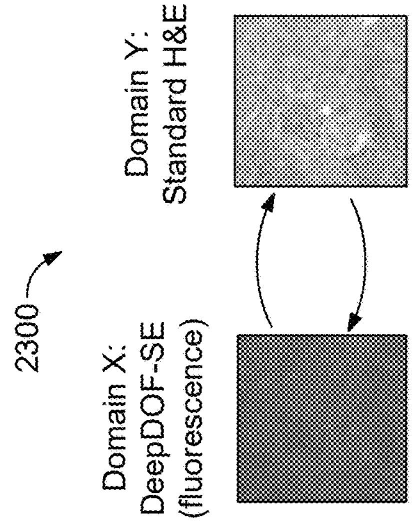
FIG. 23 shows a one-step training scheme for the second AI model.
Figure 25:
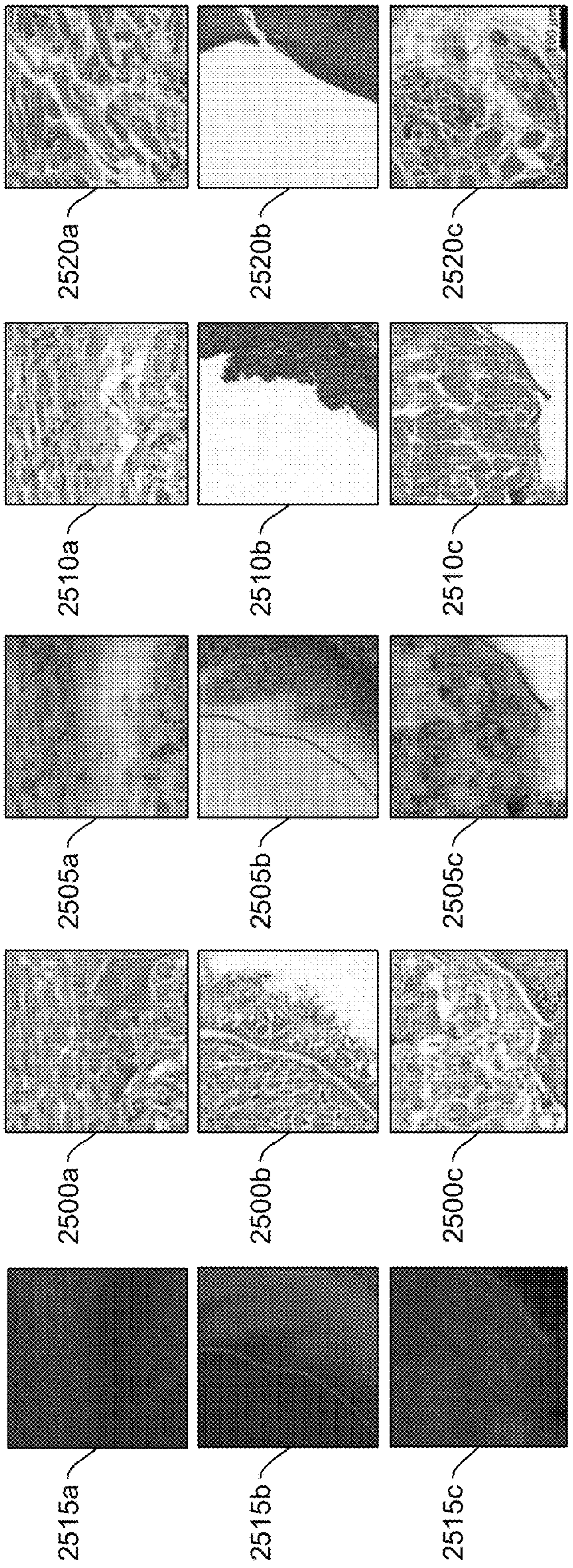
FIG. 25 displays images (far left column), virtually-stained images following the one-step training scheme for the second AI model (middle left column), virtually-stained images using the first step of the two-step training scheme for the second AI model (middle column), virtually-stained images using both steps of the two-step training scheme for the second AI model (middle right column), and comparative H&E-stained images (far right column).

The present system and method aim to train the CycleGAN so that the generators perform realistic color and texture translation while accurately preserving nuclear and counterstain features. To achieve this goal without accurately co-registered ground truth images in domains X and Y, a two-step semi-supervised training strategy was adopted (FIGS. 23 and 24). In step 1, to pretrain the generators for color translation with co-registered features, a paired training set was synthesized consisting of DeepDOF-SE images (X) and the corresponding Beer-Lambert-based false-colored H&E images (X). During this step, the generators were trained to perform the color mapping, while the feature correspondence (e.g., nuclei in DAPI channel of DeepDOF-SE images to nuclei in eosin channel in H&E images) between the two domains is preserved. In step 2, unpaired DeepDOF-SE images (X) and standard H&E images (Y) were used to retrain the CycleGAN. Compared to a CycleGAN directly trained with a dataset of unpaired images in an unsupervised manner, the semi-supervised training ensures that both nuclear and contextual features are accurately preserved (FIG. 25).

The objective used to train the GAN consists of loss terms for the generator and the discriminator in each mapping direction, and a cycle consistency loss for the two generators. More specifically, the GAN losses for the generators and discriminators are:

$$\mathcal{L}_{GAN}(G, X, Y) = \mathbb{E}_{x\sim p_{data}(x)}\left[(D_Y(G(x)) - 1)^2\right] \quad (10)$$

$$\mathcal{L}_{GAN}(D_Y, X, Y) = \mathbb{E}_{x\sim p_{data}(x)}\left[(D_Y(G(x)))^2\right] + \mathbb{E}_{y\sim p_{data}(y)}\left[(D_Y(y) - 1)^2\right] \quad (11)$$

$$\mathcal{L}_{GAN}(F, X, Y) = \mathbb{E}_{y\sim p_{data}(y)}\left[(D_X(F(y)) - 1)^2\right] \quad (12)$$

$$\mathcal{L}_{GAN}(D_X, X, Y) = \mathbb{E}_{y\sim p_{data}(y)}\left[(D_X(F(y)))^2\right] + \mathbb{E}_{x\sim p_{data}(x)}\left[(D_X(x) - 1)^2\right] \quad (13)$$

The cycle consistency loss, which ensures that the synthesized images can be mapped back to the original ground truth images through a cycle is as follows:

$$\mathcal{L}_{cyc}(G, F) = \mathbb{E}_{x\sim p_{data}(x)}[\|F(G(x)) - x\|_1] + \mathbb{E}_{y\sim p_{data}(y)}[\|G(F(y)) - y\|_1] \quad (14)$$

The cycle consistency loss is combined with the GAN losses, and as a result, the total losses for the two generators are:

$$\mathcal{L}_{total}(G, X, Y) = \mathcal{L}_{GAN}(G, X, Y) + \lambda_1 \mathcal{L}_{cyc}(G, F) \quad (15)$$

$$\mathcal{L}_{total}(F, X, Y) = \mathcal{L}_{GAN}(F, X, Y) + \lambda_1 \mathcal{L}_{cyc}(G, F) \quad (16)$$

Note that in training step 1, the standard H&E image domain Y is replaced with the Beer-Lambert-based false-colored H&E image domain ($\hat{X}$).

The CycleGAN was trained using images of resected surgical tissue from human oral cavity described above. The training dataset consists of an unpaired image dataset of 604 DeepDOF-SE images and 604 standard H&E images from the same tissue specimen. The standard H&E scans were scaled to match the DeepDOF-SE images, and a patch size of 512×512 pixels was used. For training step 1, Beer-Lambert-law-based color mapping was performed to generate paired DeepDOF-SE and false-colored images.

Once trained, the trained CycleGAN (specifically, the generator G) was evaluated for mapping DeepDOF-SE images to standard H&E images. First, its performance was validated to accurately map nuclear and cytoplasmic features between the two domains. Since it is challenging to acquire paired DeepDOF-SE and standard H&E images with co-registered features from fresh tissue specimens, frozen tissue slides of mouse tongue were used as a target. First DeepDOF-SE images of the frozen slides were obtained, which were then submitted for standard H&E processing and scanning; the H&E images were aligned to the DeepDOF-SE images through SURF feature matching to generate co-registered image pairs for algorithm validation. Once the algorithm was validated with frozen slide images, its performance was further evaluated in virtually staining DeepDOF-SE images of fresh tissue specimens.

The network was implemented using the TensorFlow package and optimized using Adam. In both steps, the CycleGAN was trained for 5 epochs, with the learning rate empirically chosen at 2e-04.

Once the tissue is resected, a pathologist cuts the specimen into 3-4 mm thick slices using a scalpel to examine the cross-section area. Suspicious slices will be sent for downstream processing.

For frozen section processing, a cryostat is used to quickly freeze the tissue and section it into thin 5-10 μm slices. In permanent H&E, the tissue is first formalin fixed and paraffin embedded (FFPE) before thin sectioning, requiring over 24 hours for processing. After the thin tissue slice is mounted onto glass slides, they are stained in batches in a slide stainer. After staining, the slide is either manually scanned by the pathologist under a conventional light microscope or scanned and digitized using a slide scanner.

In contrast, DeepDOF-SE only requires simple staining after the tissue is bread loafed into thick sections. The specimen cross section is stained with DAPI and Rhodamine B. The stained tissue is imaged using DeepDOF-SE, and the image is processed and stored on a computer. DeepDOF-SE costs only a fraction of that of other more complex systems designed for slide-free histology, such as the confocal microscope or full field OCT.

Depth-of-field range and tissue irregularity characterization. The targeted DOF of 200 μm was determined based on irregularities in the surface of thick tissue slices cut with a surgical scalpel. Per standard of care, a pathologist cuts a resected surgical specimen into 3-4 mm thick slices (bread loafing). While irregularities on the scalpel-cut surfaces exceed DOF of a conventional microscope, DeepDOF-SE is designed to directly image scalpel-cut surfaces without need for refocusing. Scalpel-cut tissue surfaces were previously reported to have surface irregularities of up to 200 μm in height. In the present study, the surface profile of porcine tongue slices cut with a pathology scalpel were characterized. With manual refocusing, the axial range of surface irregularities in 200 FOVs (each measured 0.87×0.65 $mm^2$) were recorded from four different tissue slices. The present results are consistent with previously reported results.

Regarding objective lens design choice DeepDOF-SE was specifically designed with a 4×, 0.13 NA objective to provide a slide-free histology platform for use in low-resource settings to support immediate biopsy assessment and/or rapid intraoperative assessment of margin status.

The performance of DeepDOF-SE was evaluated with a 10× 0.30 NA objective. Compared to the conventional baseline with the same objective lens, the DOF was significantly expanded from 7 microns to 40 microns (5.4× increase). However, this DOF is still far from the 200 microns required for imaging scalpel-cut irregular tissue surfaces. In this 40-micron DOF range, higher RMSE and decreased imaging performance were observed in defocus ranges of +/−15-20 microns, making it challenging to resolve features in a target 200 μm DOF range.

Figure 20:
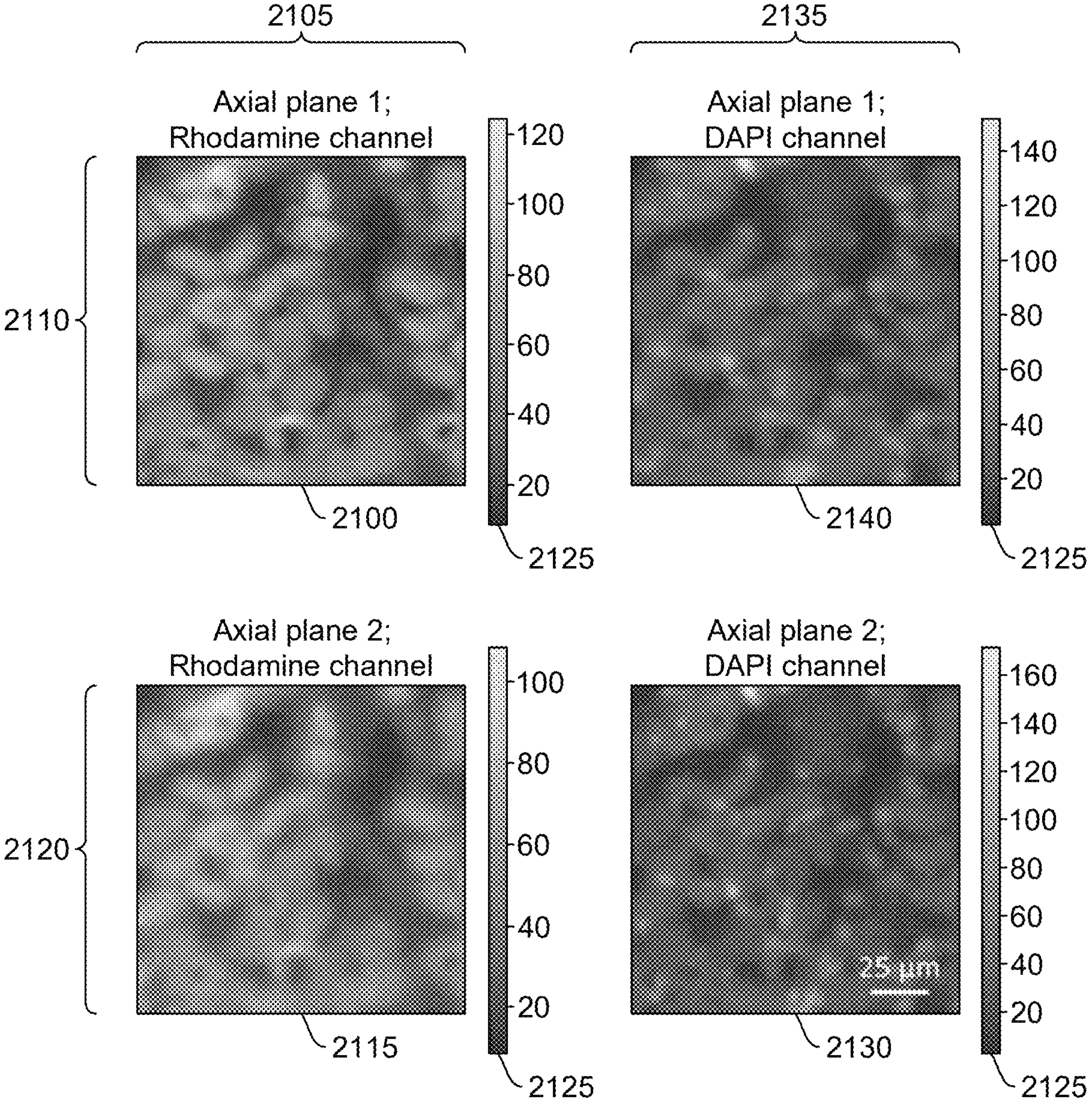
FIG. 20 displays chromatic aberrations in comparative images for two planes and two channels.

Achromaticity of the DeepDOF-SE Design. To demonstrate chromatic aberration between the two fluorescence channels, a frozen section of a mouse tongue stained with Rhodamine B and DAPI was imaged using a conventional microscope at two axial planes that are 50 μm apart. As shown in FIG. 20, image 2100 in Rhodamine channel 2105 is in focus at axial plane 1 (2110) and image 2115 is out of focus at axial plane 2 (2120) as shown by the scale bars 2125 for intensity. Image 2130 in DAPI channel 2135 is in focus at axial plane 2 (2120) and image 2140 is out of focus at axial plane 1 (2110) also shown by the scale bars 2125. In contrast to FIG. 20, DeepDOF-SE images in both channels are consistently in focus across the entire DOF 120.

While the end-to-end framework described in FIG. 2 is optimized for DAPI and Rhodamine B fluorescence channels in the current work, the feasibility of using the end-to-end framework to achieve EDOF imaging in a broadband spectral range was also explored. The DeepDOF-SE design is highly achromatic, showing that the system is widely compatible with other vital dyes and combinations of contrast agents for multiplexed imaging in multiple fluorescence channels. Here, spectral ranges in the R (640 nm), G (532 nm), and B (473 nm) channels are chosen based on the camera sensor filter.

To evaluate the achromaticity and depth-of-field of the optimized design including the learned phase mask and reconstruction networks, the modulated transfer function (MTF) of the system was simulated. For each of the 21 discrete defocus depths, a ground truth USAF resolution target is used to simulate an RGB sensor image. The simulated sensor image is then reconstructed by the U-Nets. For each color channel in the reconstructed images, the contrast of 7 line-pair (lp) groups ranging from 87 lp/mm (11.5 μm line width) to 347 lp/mm (2.9 μm line width) are calculated as follows:

$$\text{contrast}\left(img_{lp}\right) = \frac{\max\left(img_{lp}\right) - \min\left(img_{lp}\right)}{\max\left(img_{lp}\right) + \min\left(img_{lp}\right)}$$

$$\text{contrast}_{(grp\,i)} = \frac{\text{horizonatal contrast}_{grp\,i} + \text{vertical contrast}_{grp\,i}}{2}$$

The close proximity of MTFs in 3 color channels shows that the end-to-end optimized system is highly achromatic. All 3 color channels achieved high contrast in the majority of frequency ranges within the DOF. In contrast, the conventional microscope's MTF shows rapid decrease in area under the MTF curve as the defocus increases. The effects of chromatic aberration can also be observed in the separation of MTF curves. However, the forward optical model does not fully capture the aberration caused by the objective and tube lens of the experimental system.

Figure 21:
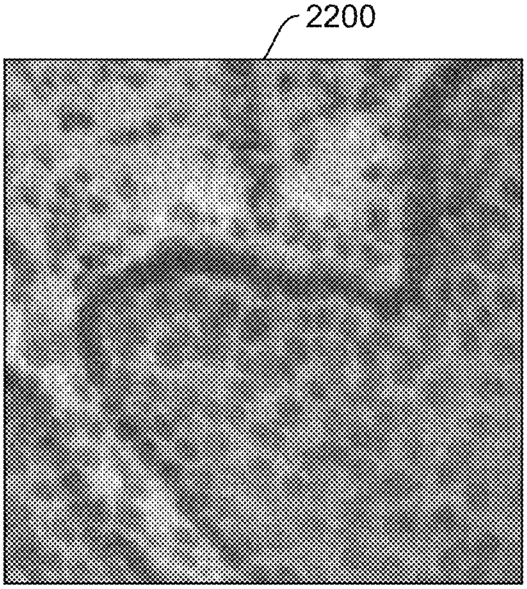
FIG. 21 displays a comparative image.

MS-SSIM calculation for frozen section slide imaging with defocus. In FIGS. 7A, 7B, 11A, 11B, 12A, and 12B, the image at 0 μm defocus was used for the respective microscopes as the ground truth when comparing the MS-SSIM across different depths. The MS-SSIM between the conventional and DeepDOF-SE at 0 μm defocus are as follows: Colon: 0.9039; esophagus: 0.8731; liver: 0.9001. As shown in FIG. 21, the conventional image 2200 has a higher noise level than DeepDOF-SE image 2205 in FIG. 22, which contributes to the discrepancy in the MS-SSIM score at 0 μm defocus.

Regularization effects of the 2-step training in CycleGAN. In order to train a CycleGAN for virtual H&E training, there are two possible models. The first model, as presented in FIG. 23, directly translates DeepDOF-SE fluorescence reconstruction into the domain of standard H&E slides. While the input requires no preprocessing, CycleGAN fails to learn the color transformation with cycle consistency loss alone. The brighter nuclei in the fluorescence image erroneously show up as white empty space in the virtual H&E. Similarly, the black background in the fluorescence input is mistaken as dark nuclei in the GAN output.

Using a semi-supervised method, these examples show that CycleGAN is in fact capable of learning the color transformation. FIG. 24 describes the 2-step training process. In step 1, CycleGAN is trained in a supervised fashion with paired fluorescence and Beer-Lambert virtual staining images. This step forces the network to learn the color transformation. In step 2, the same network is fine-tuned by replacing the DeepDOF-SE Beer-Lambert virtual H&E with the standard H&E. Although step 2 is unsupervised, CycleGAN still produces correct mapping since the network has already learned the color transformation in step 1. The final trained CycleGAN can directly map DecpDOF-SE fluorescence images to virtual H&E in a single feedforward step.

Figure 26:
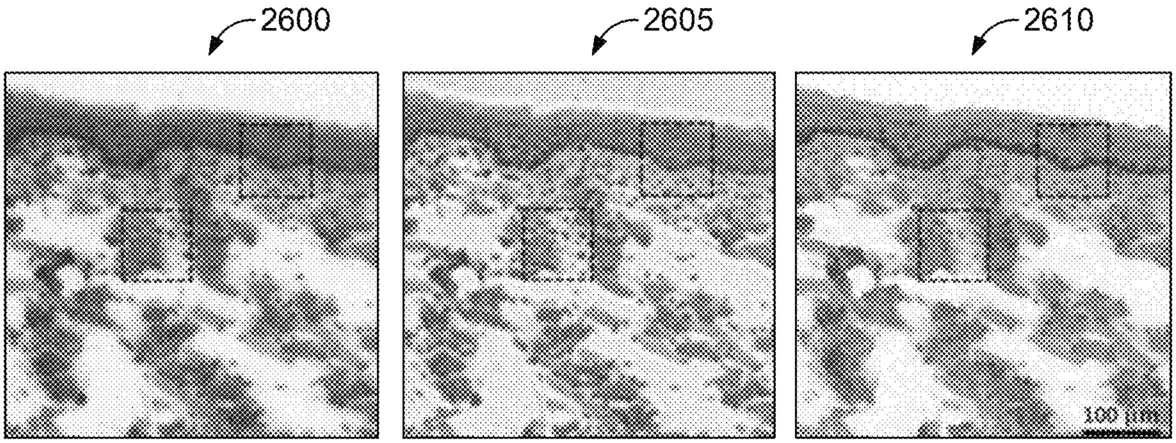
FIG. 26 displays a comparative Beer-Lambert-stained image (left), virtually-stained image (middle), and comparative H&E-stained image (right).

Quantitative comparison of Beer-Lambert, CycleGAN virtually stained tissue, and standard H&E. To validate the performance of CycleGAN virtual staining, the CycleGAN staining was quantitatively compared to standard H&E staining. Mouse tongue frozen section slides were first imaged using DeepDOF-SE, and they were sent to a pathology laboratory for conventional H&E processing. These examples empirically validated that the fluorescence staining used for DeepDOF-SE does not affect the downstream H&E processing. FIG. 26 shows the CycleGAN stained mouse tongue slide at various steps of the processing (2500*a-c*, 2505*a-c*, 2510*a-c*, and 2515*a-c*) in accordance with one or more embodiments compared to the corresponding gold standard H&E scan 2520*a-c*. While some color differences are observed, the nuclei thresholding results show that the location and shape of the nuclei in the CycleGAN virtual staining images closely resemble those in the conventional H&E images.

The results were further quantified by comparing the nuclear count and mean nuclear area in the virtually stained images (CycleGAN and Beer-Lambert-law based method) and the conventional H&E images shown in FIG. 26. The virtually stained images were warped to align with the standard H&E. The open-source software "Cell Profiler" was used to automatically segment and count the cell nuclei. Four 504×504 μm FOVs of the mouse tongue frozen section, including 2 shown in FIG. 26, are selected and the results are displayed in Table 2. The close match of both metrics between the CycleGAN staining and standard H&E demonstrates that the CycleGAN-based virtual staining provides histology information of diagnostic importance without generating undesired artifacts. The small differences in the nuclear count and nuclear area can be ascribed to the staining color differences observed in FIG. 26, errors in automated segmentation, and discarded nuclei near the FOV edges. When comparing the mean nuclear area, CycleGAN virtual staining provides a closer match than Beer-Lambert-law based method, potentially due to the closer color to the H&E resulting in better channel demixing for nuclei segmentation.

In the case of frozen section slide virtual staining, the algorithm only needs to perform color transformation since the captured image already contains slide-based features. When comparing Beer-Lambert-based virtual staining and CycleGAN staining of fresh tissue (FIGS. 27 and 28), it can be observed that the CycleGAN generates images that more closely resemble physically stained H&E slides. For instance, the white space between muscle fibers is present in both the CycleGAN virtual staining and the FFPE H&E, but not the Beer-Lambert-based staining. By learning the style of physically stained H&E slides, CycleGAN virtual staining has higher contrast and more closely resembles FFPE H&E used by pathologists.

A blinded review of histological features was conducted to further assess the diagnostic value of DeepDOF-SE images quantitatively. In this pilot evaluation, 20 DeepDOF-SE fluorescence images of fresh oral tumor resections, each containing varied histological features in a 2 mm×2 mm FOV, were obtained. These fluorescence images were processed using the Beer-Lambert-law-based method and with CycleGAN staining, resulting in a total of 40 images each covering an FOV of 4 mm$^2$. De-identified images were presented in randomized order to two expert pathologists who were asked to evaluate each image and assess the degree to which image quality was sufficient for 1) identification of architecture and normal structures, and 2) diagnosis of neoplasia. For each metric, three quality scores were used: 1=poor image quality, not sufficient for diagnosis, 2=moderate image quality but sufficient for diagnosis, and 3=good image quality, sufficient for diagnosis.

The mean image quality score was higher for images stained using CycleGAN for both pathologists. A Wilcoxon signed-rank test showed a significant difference ($Z=-2.55$, $p<0.05$ for both metrics) between scores given for Beer-Lambert-law based images and CycleGAN images.

Figure 29:
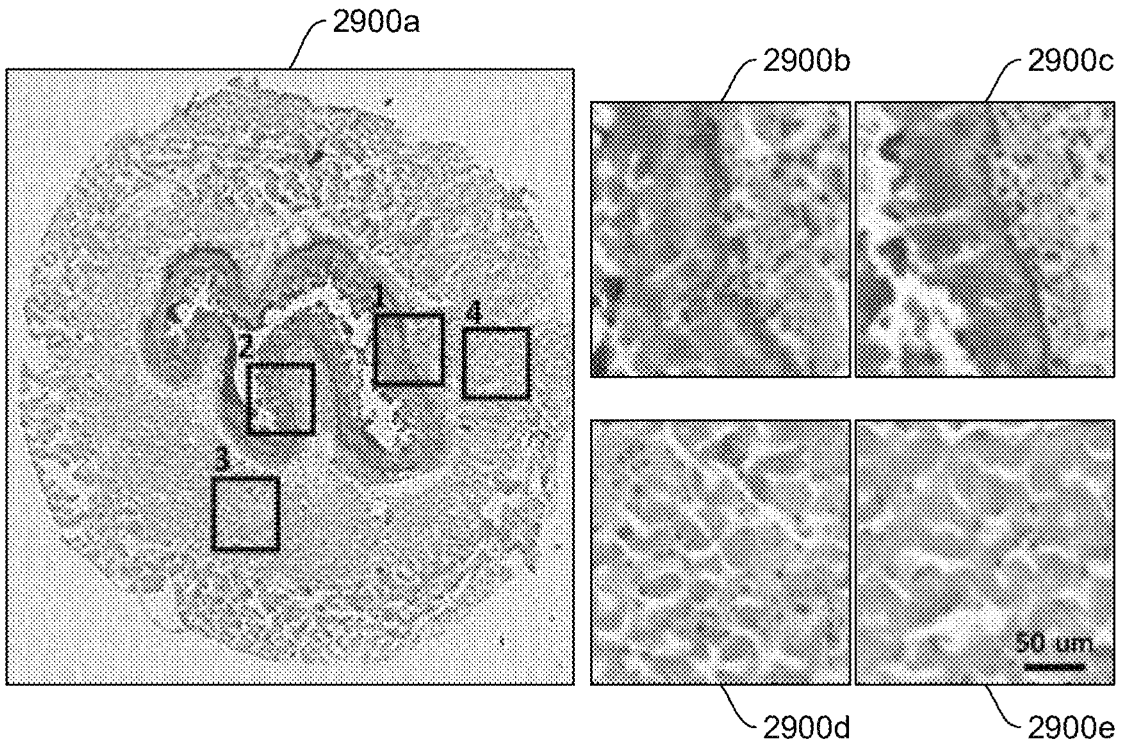
FIG. 29 displays virtually-stained images.

CycleGAN virtual staining applied to other tissue types. It is critical to validate CycleGAN performance using data not seen in the training set. Following CycleGAN training with images of fresh human oral tumor, model performance was evaluated using images from three different tissue types. Other than the mouse tongue tissue and the fresh human oral surgical samples, frozen sections of mouse esophagus were imaged. FIG. 29 shows an image of a mouse esophagus stained virtually using the CycleGAN algorithm. The image clearly shows the esophageal architecture with epithelium and surrounding connective tissue and muscle. As shown in selected ROIs, nuclei in the epithelial layer and connective tissue in the lamina propria in ROIs 1 and 2, as well as muscle fibers in ROIs 3 and 4, are visualized in the virtually stained DeepDOF-SE images. Since CycleGAN virtual staining was trained using oral tissue images, the present inventors expect improved staining performance can be achieved by training the model with an expanded image library of specific tissue types.

Figure 30:
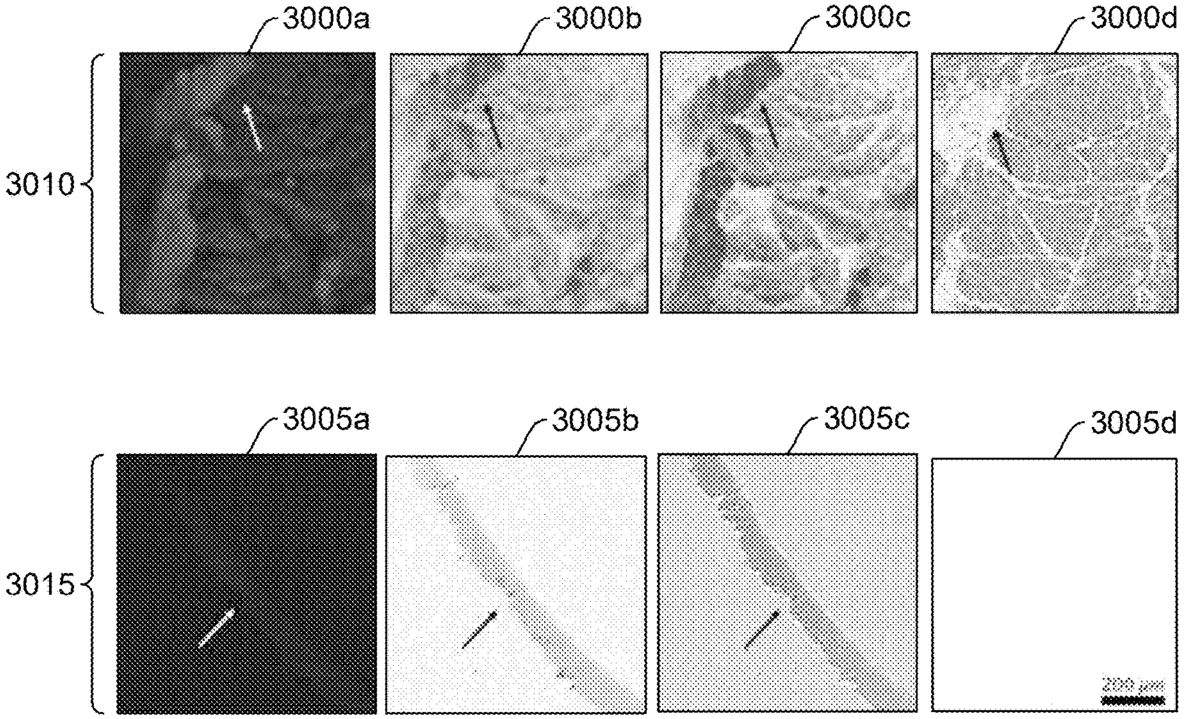
FIG. 30 displays images (far left column), Beer-Lambert-stained images (middle left column), virtually-stained images (middle right column), and comparative H&E-stained images (far right column) for a first tissue type (top row) and second tissue type (bottom row).

Exceptional cases in CycleGAN results. While the CycleGAN is capable of virtually staining various tissue types such as the layered epithelium and muscle fibers, the present inventors observed some differences between CycleGAN virtually stained images and H&E images, due to inherent differences in staining mechanisms and sample processing. In these exceptional cases, CycleGAN stains these areas similar to the analytical Beer-Lambert method, preserving features in the fluorescence images. For instance, adipose cells usually have a web-like appearance in the conventional slide-based H&E due to mechanical sectioning and loss of lipids during H&E processing. Since DeepDOF-SE images fresh tissue, adipose cells appear intact in the fluorescence images. FIG. 30 top row shows the round sphere-shaped adipose cells in the fluorescence, Beer-Lambert virtual staining, and CycleGAN virtual staining images, even though the same area shows a honeycomb architecture in the corresponding standard H&E images. Despite the visual differences, the intact adipose cells in CycleGAN stained images possess a distinct look and are readily discernable from other tissue types. The preparation of conventional H&E stained slides requires xylene exposure which removes lipids, giving adipose cells a clear appearance. When necessary to stain lipid-containing structures, pathologists routinely use Oil Red O staining. Because DeepDOF-SE examines fresh tissue, the resulting lipid staining pattern is more similar to tissue stained with Oil Red O. Because this is a stain that is commonly used in pathology, it is unlikely that it will result in interpretation challenges; it may be advantageous for evaluating certain tissue types. For example, in breast cancer, the presence of adipose cells is useful for delineating tumor margins. Additionally, residual dyes in excessive phosphate buffer solution (PBS) used to rinse the tissue post-staining may result in residual fluorescence signal; however, as shown in FIG. 30, the contour from residual dyes is far from the sample and thus does not interfere with tissue imaging.

FIG. 8 illustrates the DeepDOF-SE platform for slide-free histology of fresh tissue specimens. The DeepDOF-SE is built based on a simple fluorescence microscope with three major components: surface UV excitation that provides optical sectioning of vital-dye stained fresh tissue; a deep-learning-based phase mask and reconstruction network that extends the depth-of-field, enabling in-focus imaging of irregular tissue surfaces; and a CycleGAN that virtually stains fluorescence images resembling H&E-stained sections. Compared to a conventional fluorescence microscope, DeepDOF-SE acquires high-contrast, in-focus and virtually stained histology images of fresh tissue specimens.

FIG. 9 displays a comparative image (far left), comparative image with ultraviolet (UV) excitation (middle left), deblurred image (middle right), and virtually-stained image (far right) of an ex-vivo porcine tongue sample. The comparative image (far left) was acquired using a conventional fluorescence microscope with 405 nm excitation. The comparative image with UV excitation (middle left) was acquired using a conventional fluorescence microscope with 280 nm excitation. The deblurred image (middle right) was acquired using the DeepDOF-SE in fluorescence mode. The virtually-stained image (far right) was acquired using the DeepDOF-SE with virtual staining. Benefits of optical sectioning, extended depth-of-field, and virtual staining are shown from left to right with the addition of UV excitation, deep-learning-enabled extended DOF imaging, and CycleGAN based virtual staining. Scale bars are 100 μm. Brightness increased for display. Compared to conventional histopathology, DeepDOF-SE significantly reduces the time, infrastructure, and expertise needed to prepare histology samples. UV: ultraviolet; DOF: depth-of-field; H&E: hematoxylin and cosin; DeepDOF-SE: a deep learning enabled extended depth-of-field microscope with surface excitation.

FIG. 2 is an end-to-end deep learning network to jointly design the imaging optics and image processing for extended depth-of-field imaging in two fluorescence channels. The end-to-end (E2E) network first simulates the physics-derived image formation of a fluorescence microscope with a learned phase mask and produces simulated blurred images; then the sequential image processing layers consisting of two U-Nets reconstructs in-focus images within the targeted DOF of 200 μm. Both the phase mask design and the U-Net weights are optimized based on the loss between the ground truth images and the corresponding reconstructed images. PSF: point spread function; RMS: root mean square.

FIG. 10 displays a comparative sequence of images (bottom two rows) and sequence of images (top two rows) for a first channel (top row and middle bottom row) and second channel (middle top row and bottom row) . . . . The DeepDOF-SE microscope is built based on a simple fluorescence microscope, with the addition of a deep-learning-enabled phase mask that enables an extended DOF and a UVC LED that enables surface excitation. Experimentally captured point spread functions at 21 discrete depths within the 200 μm target DOF. Experimental resolution characterization of the spatial resolution of DeepDOF-SE in DAPI and Rhodamine B channels using a USAF 1951 resolution target, in comparison to a conventional fluorescence microscope as the baseline. DeepDOF-SE consistently resolves Group 7, element 5 (2.46 μm line width) or better in both color channels within the target DOF; in addition, DeepDOF-SE exhibits significantly reduced chromatic aberration compared to the conventional microscope.

Figure 11A:
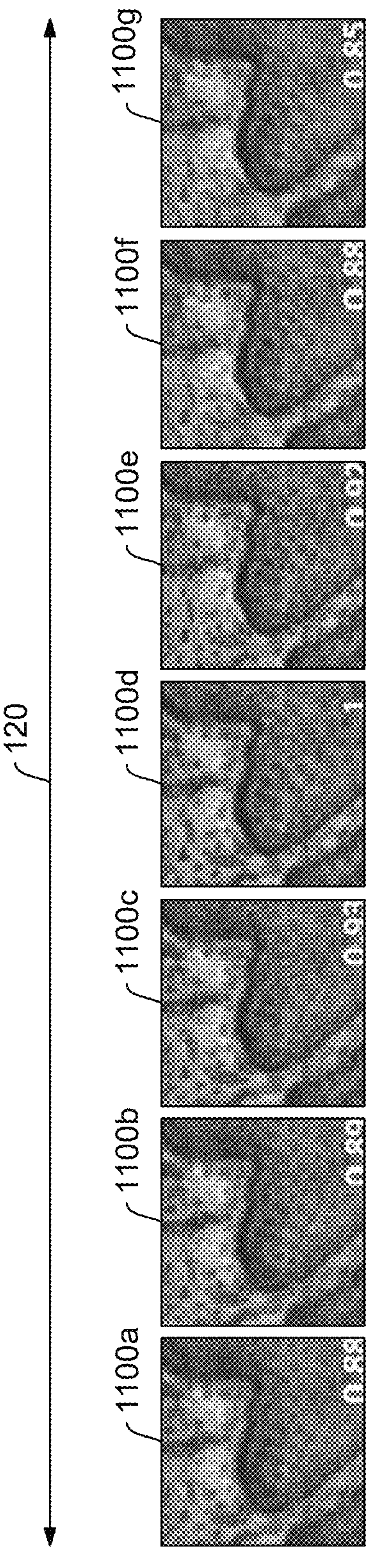
FIG. 11A displays a sequence of deblurred images.
Figure 11B:
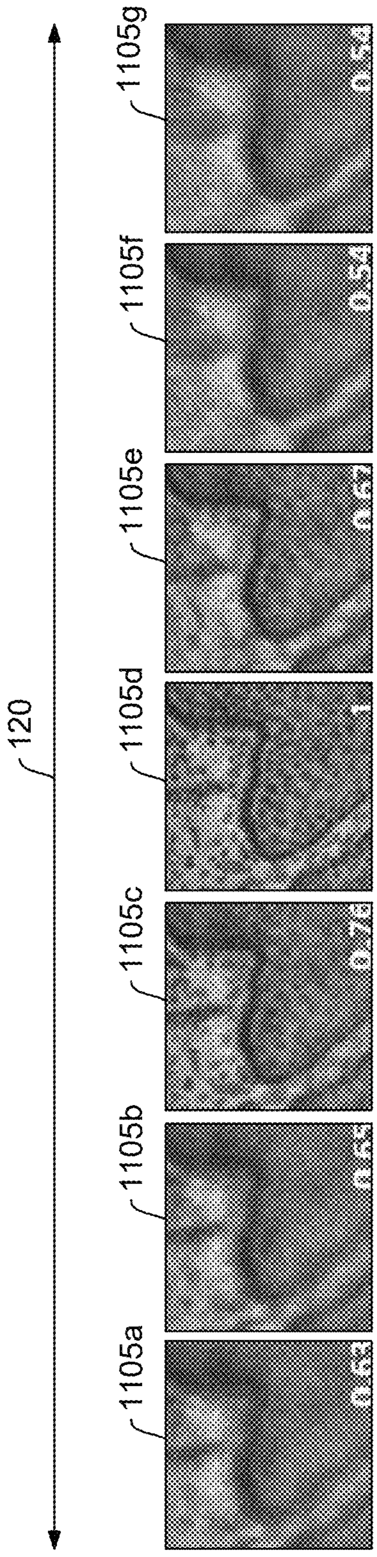
FIG. 11B displays a comparative sequence of images.
Figure 12A:
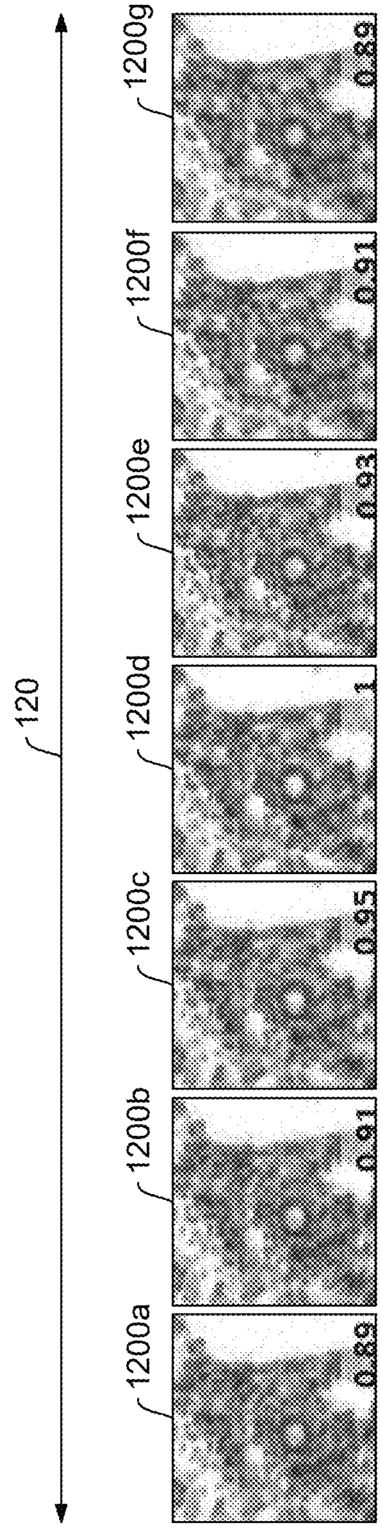
FIG. 12A displays a sequence of deblurred images.
Figure 12B:
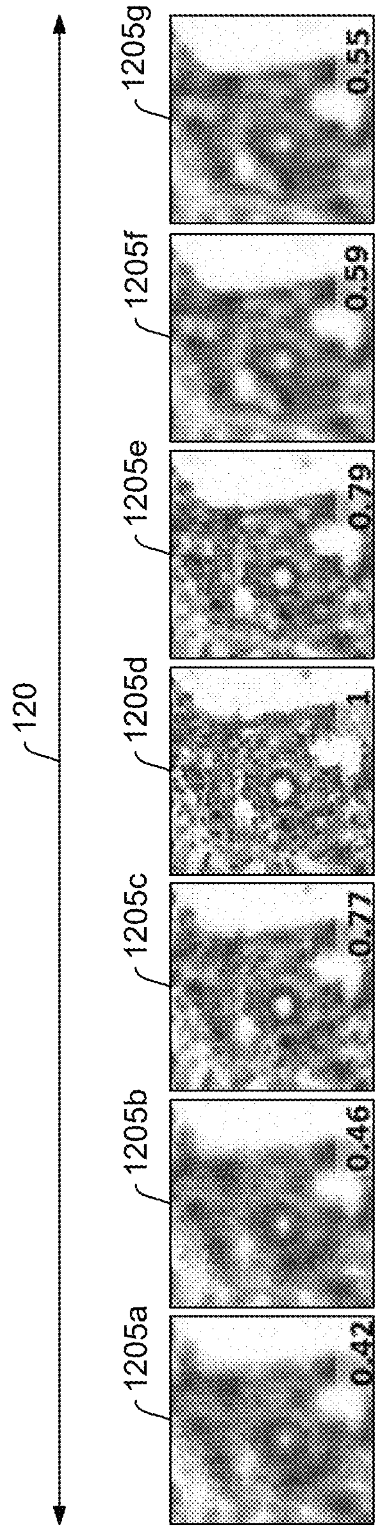
FIG. 12B displays a comparative sequence of images.

FIGS. 11A and 12A display a sequence of deblurred images of thin (7-10 μm) frozen tissue sections of varied types acquired with DeepDOF-SE (i.e., images 1100*a-g* and 1200*a-g*). FIGS. 11B and 12B display a comparative sequence of images imaged using a conventional microscope (i.e., images 1105*a-g* and 1205*a-g*). Each image of the sample is translated axially throughout the target DOF 120. All images are virtually stained using the Beer-Lambert method, an analytical color space transform to better visualize the subcellular features while preserving defocus artifacts. Virtually stained images from human tissue sections revealed architectural and cellular morphology of colonic crypts lined by intestinal columnar epithelium (top panel), esophagus lined by stratified squamous epithelium (middle panel), and bile duct and portal vein within the portal tract of the liver (bottom panel). In all tissue types, cell nuclei are consistently resolved in images acquired with DeepDOF-SE, while significant defocus blur was observed in images acquired with the conventional microscope. The multiscale structural similarity index MS-SSIM was consistent as the sample was translated throughout the DOF of DeepDOF-SE, while the MS-SSIM dropped rapidly as the sample was translated across the focal plane of the conventional microscope. Scale bars are 100 μm. MS-SSIM: multiscale structural similarity index measure.

Each of FIGS. 13 and 14 displays images (bottom row) and comparative images (top row) of intact fresh tissue of varied types. The images (bottom rows) are obtained using DeepDOF-SE. The comparative images (top rows) are obtained using a conventional microscope without refocusing. Conventional*: Conventional microscope (4× 0.13 NA) with 280 nm excitation, with virtual staining using the Beer-Lambert method; DeepDOF-SEt: DeepDOF-SE microscope, with virtual staining using the Beer-Lambert method. Ex-vivo porcine kidney sample with five annotated ROIs. Conventional microscope images from ROIs 1-3 are out-of-focus while ROIs 4 and 5 are in focus. Corresponding DeepDOF-SE images are in focus for all ROIs. Ex-vivo human tongue resection with five annotated ROIs. Conventional microscopy images from ROIs 6-8 are out-of-focus while ROIs 9-10 are in focus. Corresponding DeepDOF-SE images are in focus for all ROIS. ROI scale bars are 50 μm.

FIG. 15 illustrates the CycleGAN architecture in accordance with one or more embodiments. The image-to-image mapping network G is trained to virtually stain DeepDOF-SE images using a semi-supervised training strategy without paired DeepDOF-SE images and standard H&E images. FIG. 16 displays virtually-stained images (top left, left column, and middle right column) and comparative H&E-stained images (top right, middle left column, and right column) for a first field of view of a frozen section of mouse tongue frozen section. FIG. 17 displays virtually-stained images (top left, left column, and middle right column) and comparative H&E-stained images (top right, middle left column, and right column) for a second field of view of a frozen section of mouse tongue frozen section. Each FOV is 504×504 μm. Insets demonstrate accurate staining of nuclear and cytoplasmic features. Scale bar: 100 μm.

Each of FIGS. 18 and 19 displays images (top row), virtually-stained images (middle row), and comparative H&E-stained images (bottom row) of oral surgical specimens, specifically, ex-vivo human tongue resections. Deep- DOF-SE visualizes a broad range of important diagnostic features that are consistent with the gold standard H&E. ROI 1: Epithelial hyperplasia with dysplasia. ROI 2: Epithelial hyperkeratosis and hyperplasia with dysplasia. ROIs 3 and 4: Skeletal muscle bundles. ROIs 5 and 6: Epithelial hyperkeratosis and hyperplasia. ROI 7: Invasive squamous cell carcinoma with dyskeratosis. ROI 8: Muscular artery. FFPE: formalin-fixed and paraffin-embedded; H&E: hematoxylin and eosin.

The slide-free DeepDOF-SE requires less equipment, simplified procedures, and shorter time, altogether leading to ease of use and reduced cost. FIG. created with Biorender.com.

FIG. 20 displays chromatic aberrations in comparative images for two planes and two channels of mouse tongue frozen slides acquired using a conventional microscope, showing chromatic aberrations observed in two fluorescence channels at two axial planes (axial planes 1 and 2 are 50 μm apart). The image in Rhodamine channel is in focus at axial plane 1, while the image in DAPI channel is in focus at axial plane 2.

Figure 22:
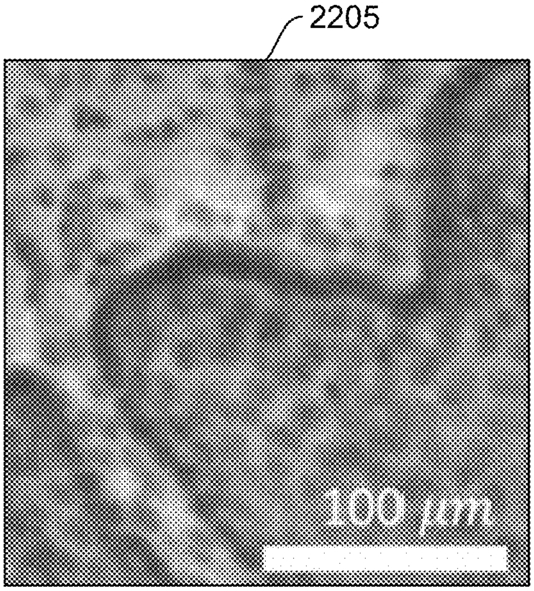
FIG. 22 displays an exemplary image.

FIG. 21 displays a comparative image of a frozen section slide of human esophagus at 0-micron defocus. FIG. 22 displays an image of a frozen section slide of human esophagus in accordance with one or more embodiments at 0-micron defocus. The MS-SSIM between the two field-of-view is 0.8731. The proposed DeepDOF-SE is able to resolve the nuclei as well as the in-focus conventional while appearing less noisy.

FIG. 23 shows a one-step training scheme 2300 for the second AI model in accordance with one or more embodiments. FIG. 24 shows a two-step training scheme 2400 for the second AI model in accordance with one or more embodiments. The one-step unsupervised training that directly translates fluorescence DeepDOF-SE images to standard H&E. The two-step semi-supervised training: in step 1, paired DeepDOF-SE fluorescence and DeepDOF-SE Beer-Lambert virtual H&E is used to train the CycleGAN (supervised); in step 2, the same CycleGAN weights are fine-tuned by replacing the DeepDOF-SE Beer-Lambert virtual H&E with the standard H&E (unsupervised). Rhodamine B channel for the fluorescence image brightened for display.

FIG. 25 displays images (far left column), virtually-stained images following the one-step training scheme for the second AI model (middle left column), virtually-stained images using the first step of the two-step training scheme for the second AI model (middle column), virtually-stained images using both steps of the two-step training scheme for the second AI model (middle right column), and comparative H&E-stained images (far right column). The bright blue nuclei in the fluorescence images 2515*a-c* are incorrectly translated to white space in the one-step CycleGAN 2505, as the network fails to learn the color translation. Step 1 of the two-step training scheme forces the CycleGAN to learn the color transform (column 3 from the left). After the two-step training, the CycleGAN is able to translate with both the color and style of the standard H&E correctly (column 4 from the left).

FIG. 26 displays a comparative Beer-Lambert-stained image 2600 (left), virtually-stained image 2605 (middle), and comparative H&E-stained image 2610 (right) of frozen section mouse tongue slide of the same slide. The large FOVs are 504×504 μm and correspond to the FOV1 and FOV2 in Table 3 respectively.

Table 3 shows nuclei count and mean nuclear area comparison between CycleGAN virtually stained and standard H&E images of mouse tongue frozen section. Each FOV is 504×504 μm. FOV1 and FOV2 are shown in FIGS. 16 and 17 and FIG. 26.

Figure 27:
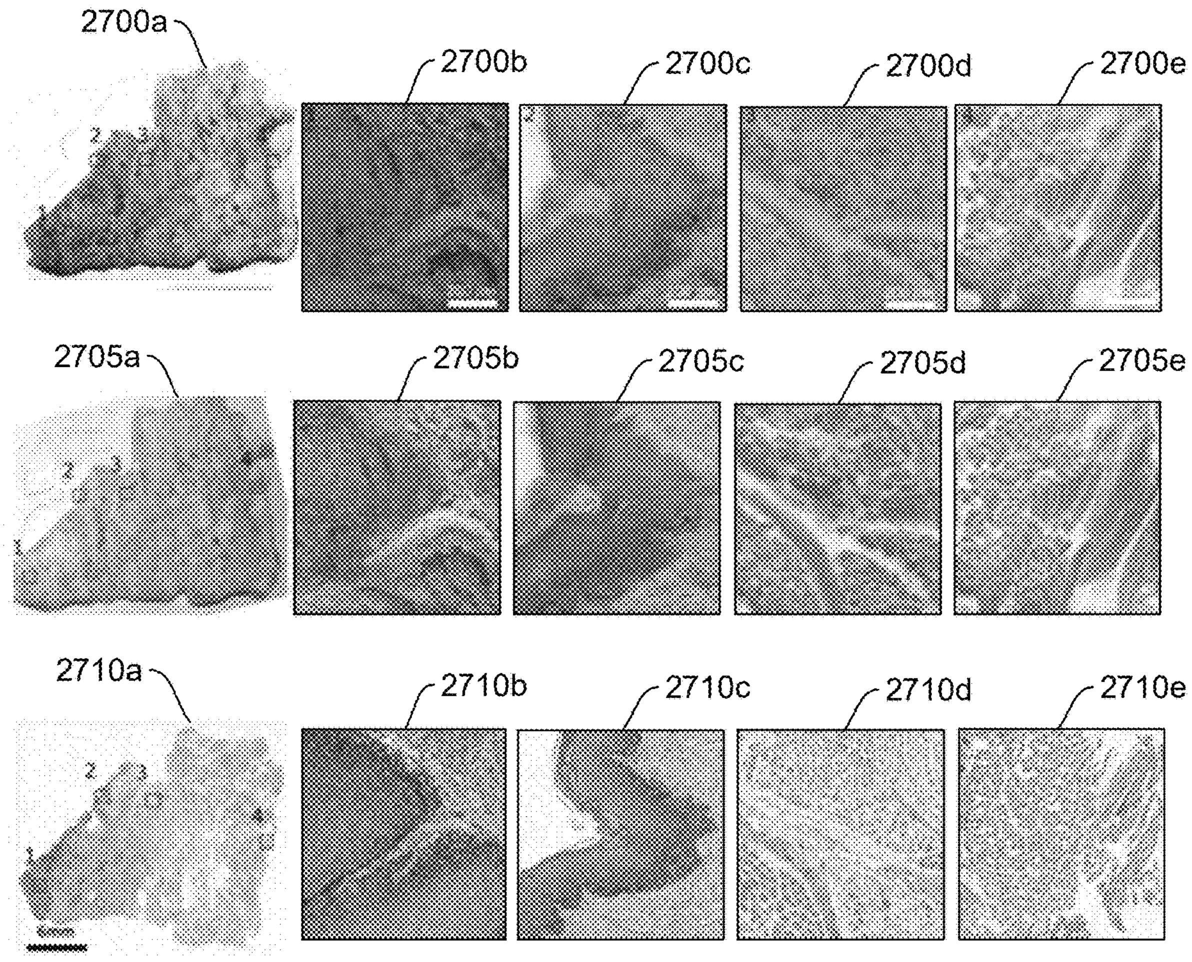
FIG. 27 displays Beer-Lambert-stained images (top row), virtually-stained images (middle row), and comparative H&E-stained images (bottom row).
Figure 28:
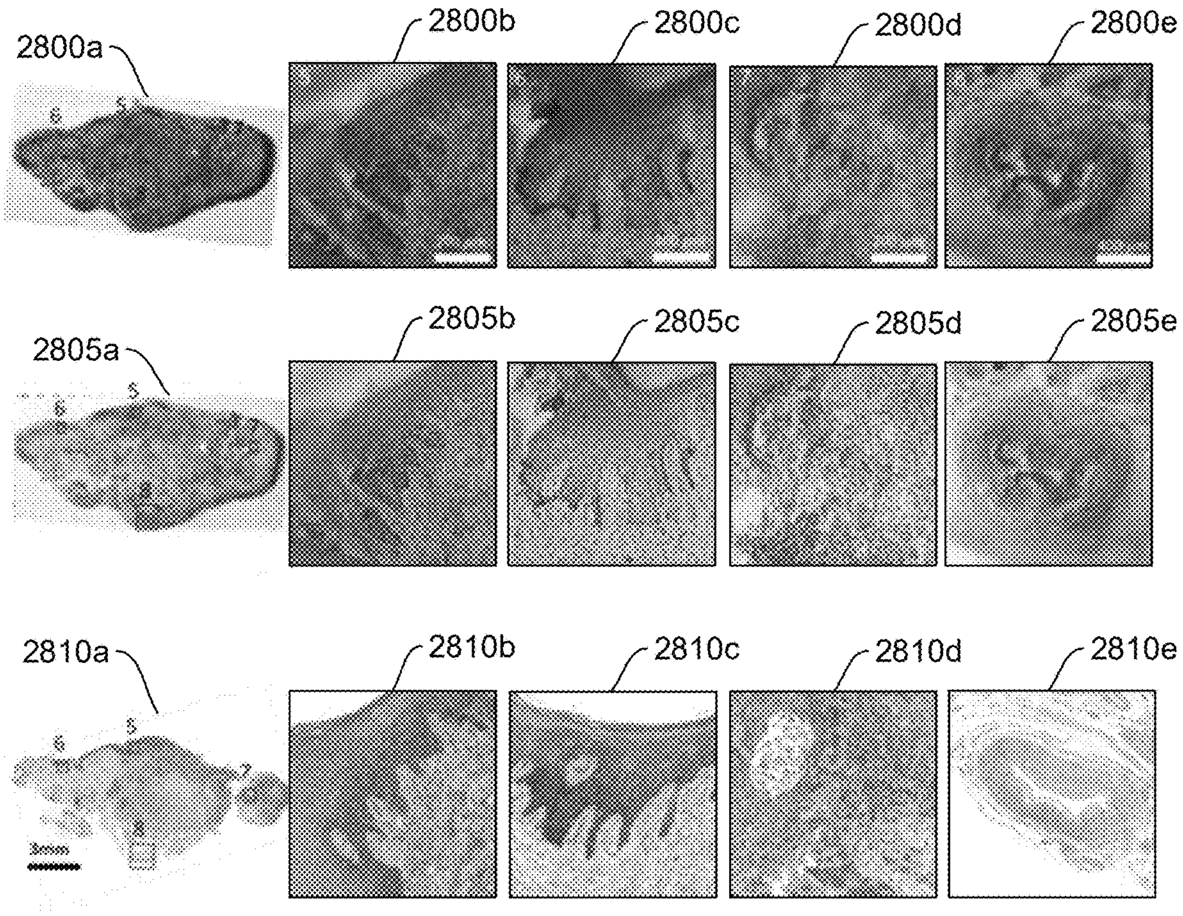
FIG. 28 displays Beer-Lambert-stained images (top row), virtually-stained images (middle row), and comparative H&E-stained images (bottom row).

FIGS. 27 and 28 show the same tissue as FIGS. 18 and 19, replacing DeepDOF-SE fluorescence with DeepDOF-SE Beer-Lambert virtual staining to show the comparison between Beer-Lambert H&E and CycleGAN H&E. In other words, each of FIGS. 27 and 28 display Beer-Lambert-stained images (2700*a-e* and 2800*a-e*) (top row), virtually-stained images (2705*a-e* and 2805*a-e*) (middle row), and comparative H&E-stained images (2710*a-e* and 2810*a-e*) (bottom row). In both samples, the CycleGAN virtual H&E's color appears closer to the standard FFPE H&E. The CycleGAN H&E also learns the style of the thin cut slide where regions with no tissue appear white.

FIG. 29 shows a virtually-stained image 2900*a-e* of a frozen slide of mouse esophagus in accordance with one or more embodiments. Nuclei in the epithelial layer and connective tissue in the lamina propria in images 2900*b, c*, as well as muscle fibers in images 2900*d, c*, are visualized in the DeepDOF-SE image.

FIG. 30 displays images (3000*a* and 3005*a*) (far left column), Beer-Lambert-stained images (3000*b* and 3005*b*) (middle left column), virtually-stained images (3000*c* and 3005*c*) (middle right column), and comparative H&E-stained images (3000*d* and 3005*d*) (far right column) for a first tissue type 3010 (top row) and second tissue type 3015 (bottom row) in accordance with one or more embodiments. These are exceptional cases where the CycleGAN virtually-stained images (3000*c* and 3005*c*) do not resemble the standard H&E images (3000*d* and 3005*d*). These images are compared to fluorescence images (3000*a* and 3005*a*) and standard H&E images (3000*d* and 3005*d*). Top row 3010: Adipose cells appear intact in the DeepDOF-SE image 3000*c*, while in the conventional H&E image 3000*d*, the cells' cytoplasmic lipids are lost due to H&E sectioning and processing. Bottom row 3015: residual fluorescence from residual rinsing buffer is imaged by DeepDOF-SE image 3005*c*, which does not occur in slide-based H&E processing imaging 3005*d*. This artifact is far away from the tissue and can be easily discerned.

What is claimed is:

1. A system comprising:

a microscope comprising a camera, a phase mask, and an ultraviolet source,
  wherein the phase mask is disposed within a view of the camera, and
  wherein the microscope is configured to:
    scatter a light illuminating a tissue by emitting, using the ultraviolet source, an ultraviolet radiation towards the tissue,
      wherein the tissue comprises at least one diagnostic feature; and
    obtain, using the phase mask and the camera, an image of an illuminated surface of the tissue,
      wherein the image is within a predefined depth of field, inclusive, and
      wherein the image comprises a manifestation of the at least one diagnostic feature; and
a computer system communicably coupled to the microscope and configured to:
  determine a deblurred image from a trained first artificial intelligence model based on the image, and
  determine a virtually-stained image from a trained second artificial intelligence model based on the deblurred image.

2. The system of claim 1, wherein the microscope comprises a dual-channel microscope.

3. The system of claim 1, wherein the system does not comprise a microtome configured to section the tissue.

4. The system of claim 1, wherein the system does not comprise a slide scanner communicably coupled to the microscope and the computer system.

5. The system of claim 1, wherein the phase mask is configured to deblur, at least in part, the image.

6. The system of claim 1, wherein the first artificial intelligence model is trained to determine the deblurred image based on the at least one diagnostic feature fluorescing at a predefined wavelength.

7. The system of claim 1, wherein the microscope further comprises a light source configured to emit the light towards the tissue.

8. The system of claim 1, wherein the first artificial intelligence model is trained to determine a height map of the phase mask.

9. A method comprising:

scattering, using a microscope, a lightilluminatinga tissue by emitting, using an ultraviolet source of the microscope, an ultraviolet radiation towards the tissue, wherein the tissue comprises at least one diagnostic feature;

obtaining, using a phase mask and a camera of the microscope, an image of an illuminated surface of the tissue, wherein the image is within a predefined depth of field, inclusive, and wherein the image comprises a manifestation of the at least one diagnostic feature;

determining, using a computer system, a deblurred image from a trained first artificial intelligence model based on the image; and determining, using the computer system, a virtually-stained image from a trained second artificial intelligence model based on the deblurred image, wherein the manifestation of the at least one diagnostic feature is virtually stained.

10. The method of claim 9, further comprising identifying the manifestation of the at least one diagnostic feature within the virtually-stained image.

11. The method of claim 10, further comprising diagnosing a patient of the tissue based on the manifestation of the at least one diagnostic feature.

12. The method of claim 9, wherein the tissue comprises a resected tissue.

13. The method of claim 9, further comprising applying a stain to the tissue.

14. The method of claim 13, wherein the first artificial intelligence model is trained to determine the deblurred image based on the stain fluorescing at a predefined wavelength.

15. The method of claim 9, wherein the predefined depth of field is-200 micrometers to 200 micrometers, inclusive.

* * * * *